United States Patent
Dudley et al.

(10) Patent No.: US 8,835,393 B2
(45) Date of Patent: Sep. 16, 2014

(54) INHIBITORS OF IAP

(75) Inventors: Danette Dudley, Pacifica, CA (US); John A. Flygare, Burlingame, CA (US); Chudi Ndubaku, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 43 days.

(21) Appl. No.: 13/057,176

(22) PCT Filed: Jul. 23, 2009

(86) PCT No.: PCT/US2009/051522
§ 371 (c)(1),
(2), (4) Date: Apr. 14, 2011

(87) PCT Pub. No.: WO2010/017035
PCT Pub. Date: Feb. 11, 2010

(65) Prior Publication Data
US 2011/0269696 A1    Nov. 3, 2011

Related U.S. Application Data
(60) Provisional application No. 61/085,844, filed on Aug. 2, 2008.

(51) Int. Cl.
| | |
|---|---|
| A61K 38/06 | (2006.01) |
| C07K 5/08 | (2006.01) |
| A61P 35/00 | (2006.01) |
| C07D 403/12 | (2006.01) |
| C07D 513/04 | (2006.01) |
| C07D 207/16 | (2006.01) |
| C07K 5/083 | (2006.01) |

(52) U.S. Cl.
CPC ............ *C07D 403/12* (2013.01); *C07D 513/04* (2013.01); *C07D 207/16* (2013.01); *C07K 5/0804* (2013.01)
USPC ......................................... 514/18.9; 530/331

(58) Field of Classification Search
None
See application file for complete search history.

(56) References Cited

U.S. PATENT DOCUMENTS

| | | | |
|---|---|---|---|
| 4,149,003 A | 4/1979 | Carlsson et al. | |
| 4,278,793 A | 7/1981 | Durckheimer et al. | |
| 4,720,484 A | 1/1988 | Vincent et al. | |
| 4,837,165 A | 6/1989 | Hawke | |
| 4,935,494 A | 6/1990 | Miller | |
| 5,278,148 A * | 1/1994 | Branca et al. ................. | 514/15.7 |
| 5,411,942 A | 5/1995 | Widmer et al. | |
| 5,559,209 A | 9/1996 | Nishimoto | |
| 5,998,470 A | 12/1999 | Halbert et al. | |
| 6,472,172 B1 | 10/2002 | Deng et al. | |
| 6,608,026 B1 | 8/2003 | Wang et al. | |
| 6,992,063 B2 | 1/2006 | Shi | |
| 7,041,784 B2 | 5/2006 | Wang et al. | |
| 7,067,274 B2 | 6/2006 | Fairbrother et al. | |
| 7,244,851 B2 | 7/2007 | Cohen et al. | |
| 8,110,568 B2 | 2/2012 | Cohen et al. | |
| 8,247,557 B2 | 8/2012 | Koehler et al. | |
| 2002/0177557 A1 | 11/2002 | Shi | |
| 2003/0157522 A1 | 8/2003 | Boudreault et al. | |
| 2004/0171554 A1 | 9/2004 | Franklin et al. | |
| 2005/0197403 A1 | 9/2005 | Harran et al. | |
| 2005/0214802 A1 | 9/2005 | Fairbrother et al. | |
| 2005/0234042 A1 | 10/2005 | Palermo et al. | |
| 2006/0014700 A1 | 1/2006 | Cohen et al. | |
| 2006/0052311 A1 | 3/2006 | Sharma et al. | |
| 2006/0194741 A1 | 8/2006 | Condon et al. | |
| 2007/0093428 A1 | 4/2007 | Laurent | |
| 2007/0299052 A1 | 12/2007 | Cohen et al. | |
| 2008/0050336 A1 | 2/2008 | Bachand et al. | |
| 2009/0318409 A1 | 12/2009 | Cohen et al. | |

(Continued)

FOREIGN PATENT DOCUMENTS

| | | |
|---|---|---|
| EP | 1 836 201 B1 | 9/2007 |
| JP | 2006-501181 | 1/2006 |

(Continued)

OTHER PUBLICATIONS

U.S. Appl. No. 60/560,186, filed Apr. 7, 2004, Palermo et al.
Arn et al., "Synthetic Smac/DIABLO Peptides Enhance the Effects of Chemotherapeutic Agents by Binding XIAP and cIAP1 in Situ" J Biol Chem 277(46):44236-44243 (Nov. 2002).
Baktiar et al., "Transfer of alkoxycarbonyl from alkyl imidazolium-2-carboxylates to benzyl alcohol, a cyclohexanone enamine and diethylamine" J Chem Soc Perkin Trans 1 3:329-243 (Jan. 1994).

(Continued)

*Primary Examiner* — Julie Ha
*Assistant Examiner* — Li Ni Komatsu
(74) *Attorney, Agent, or Firm* — Morrison & Foerster LLP

(57) ABSTRACT

The invention provides novel compounds that are inhibitors of IAPs having the general formula: wherein $X_1$, $X_2$, $X_3$, Y, A, $R_1$, $R_2$, $R_3$, $R_4$, $R_{4'}$, $R_5$, $R_{5'}$, $R_6$ and $R_{6'}$ are as described herein. The compounds of the invention may be used to induce apoptosis in cells (or sensitise cells to apoptosis) in which IAPs are overexpressed or otherwise implicated in resistance to normal apoptotic processes. Accordingly, the compounds may be provided in pharmaceutically acceptable compositions and used for the treatment cancers.

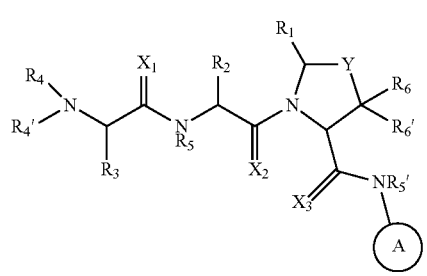

12 Claims, No Drawings

(56) References Cited

U.S. PATENT DOCUMENTS

| | | |
|---|---|---|
| 2010/0256115 A1 | 10/2010 | Cohen et al. |
| 2011/0046066 A1 | 2/2011 | Ndubaku et al. |
| 2011/0077265 A1 | 3/2011 | Flygare et al. |
| 2011/0218211 A1 | 9/2011 | Bergeron et al. |
| 2012/0015974 A1 | 1/2012 | Koehler |
| 2012/0202750 A1 | 8/2012 | Cohen et al. |
| 2012/0270886 A1 | 10/2012 | Koehler et al. |

FOREIGN PATENT DOCUMENTS

| | | |
|---|---|---|
| JP | 2009-532544 | 9/2009 |
| JP | 2009-545613 A | 12/2009 |
| JP | 2010-506847 A | 3/2010 |
| RU | 2291154 C2 | 1/2007 |
| WO | 92/01938 | 2/1992 |
| WO | WO-94/11026 A2 | 5/1994 |
| WO | WO-94/11026 A3 | 5/1994 |
| WO | WO-94/11026 C1 | 5/1994 |
| WO | 98/46597 | 10/1998 |
| WO | 00/00823 | 1/2000 |
| WO | 00/39585 A1 | 7/2000 |
| WO | 02/16402 A2 | 2/2002 |
| WO | 02/16402 A3 | 2/2002 |
| WO | 02/16418 A2 | 2/2002 |
| WO | 02/16418 A3 | 2/2002 |
| WO | 02/26775 A2 | 4/2002 |
| WO | 02/26775 A3 | 4/2002 |
| WO | 02/30959 A2 | 4/2002 |
| WO | 02/30959 A3 | 4/2002 |
| WO | WO-02/085897 A1 | 10/2002 |
| WO | 02/096930 A2 | 12/2002 |
| WO | 02/096930 A3 | 12/2002 |
| WO | 03/010184 A2 | 2/2003 |
| WO | 03/010184 A3 | 2/2003 |
| WO | 03/086470 A2 | 10/2003 |
| WO | 03/086470 A3 | 10/2003 |
| WO | 2004/005248 A1 | 1/2004 |
| WO | 2004/007529 A2 | 1/2004 |
| WO | 2004/007529 A3 | 1/2004 |
| WO | 2004/017991 A1 | 3/2004 |
| WO | 2004/072641 A1 | 8/2004 |
| WO | 2004/106371 A1 | 12/2004 |
| WO | 2005/049853 A2 | 6/2005 |
| WO | 2005/069888 A2 | 8/2005 |
| WO | 2005/069894 A2 | 8/2005 |
| WO | 2005/097791 A1 | 10/2005 |
| WO | WO-2005/094818 A1 | 10/2005 |
| WO | 2006/014361 A1 | 2/2006 |
| WO | 2006/017295 A2 | 2/2006 |
| WO | 2006/020060 A2 | 2/2006 |
| WO | 2006/020060 A3 | 2/2006 |
| WO | WO-2006/069063 A1 | 6/2006 |
| WO | WO-2006/091972 A2 | 8/2006 |
| WO | WO-2006/091972 A3 | 8/2006 |
| WO | WO-2006/122408 A1 | 11/2006 |
| WO | WO-2006/122408 C1 | 11/2006 |
| WO | 2007/048224 A1 | 5/2007 |
| WO | 2007/104162 A1 | 9/2007 |
| WO | WO-2007/106192 A2 | 9/2007 |
| WO | WO-2007/106192 A3 | 9/2007 |
| WO | 2007/136921 A2 | 11/2007 |
| WO | WO-2008/014238 A2 | 1/2008 |
| WO | WO-2008/014238 A3 | 1/2008 |
| WO | 2008/016893 | 2/2008 |
| WO | WO-2008/016893 A1 | 2/2008 |
| WO | WO-2008/045905 A1 | 4/2008 |

OTHER PUBLICATIONS

Blass et al., "Parallel Synthesis and Evaluation of N-(1-Phenylethyl)-5-phenyl-imidazole-2-amines as Na+/K+ ATPase inhibitors" Bioorg Med Chem Lett 10:1543-1545 ( 2000).
Boatright et al., "A Unified Model for Apical Caspase Activation" Mol Cell 11:529-541 ( 2003).
Chai et al., "Structural and biochemical basis of apoptotic activation by SMAC/Diablo" Nature 406(6798):855-862 (Aug. 24, 2000).
Chen et al., "grim, a novel cell death gene in *Drosophila*" Gene Dev 10:1773-1782 ( 1996).
Christich et al., "The Damage-Responsive *Drosophila* Gene sickle Encodes a Novel IAP Binding Protein Similar to but Distinct from reaper, grim, and hid" Curr Biol 12:137-140 ( 2002).
International Preliminary Report on Patentability for International Patent Application No. PCT/US2009/051522.
Notice of Opposition to European Patent No. EP1836201.
Corey et al., "(+)-1(S), 5(R), 8(S)-phenyl-2-azabicyclo[3.3.0]OCTAN-8-0L N, O-methylboronate (2) and its enantiomer, chiral chemzymes which serve as catalysts for their own enantioselective synthesis" Tetrahedron Lett 30(41):5547-5550 ( 1989).
Crook et al., "An Apoptosis-Inhibiting Baculovirus Gene with a Zinc Finger-Like Motif" J Virol 67(4):2168-2174 (Apr. 1993).
Derossi et al., "Trojan Peptides: The Penetratin System for Intracellular Delivery" Trends Cell Biol 8:84-87 (Feb. 1998).
Deveraux et al., "Endogenous Inhibitors of Caspases" J Clin Immunol 19(6):388-398 ( 1999).
Deveraux et al., "IAP family proteins-suppressors of apoptosis" Gene Dev 13:239-252 ( 1999).
Deveraux et al., "IAPs Block Apoptotic Events Induced by Caspase-8 and Cytochrome c by Direct Inhibition of Distinct Caspases" EMBO J 17(8):2215-2223 ( 1998).
Duckett et al., "A Conserved Family of Cellular Genes Related to the Baculovirus iap Gene and Encoding Apoptosis Inhibitors" EMBO J 15(11):2685-2694 ( 1996).
E-mail Relating to Date of Publication D16 (Maybridge Medchem, Bioisosteres in Medicinal Chemistry.
Fong et al., "Expression and genetic analysis of XIAP-associated factor 1 (XAF1) in cancer cell lines" Genomics 70:113-122 ( 2000).
Franklin et al., "Structure and Function Analysis of Peptide Antagonists of Melanoma Inhibitor of Apoptosis (ML-IAP)" Biochemistry 42:8223-8231 ( 2003).
Fulda et al., "Smac Agonists Sensitize for Apo2L/TRAIL- or Anticancer Drug-Induced Apoptosis and Induce Regression of Malignant Glioma in Vivo" Nat Med 8(8):808-815 (Aug. 2002).
Gordon et al., "Peptide Azoles: A New Class of Biologically-Active Dipeptide Mimetics" Bioorg Med Chem Lett 3(5):915-920 ( 1993).
Goyal et al., "Induction of apoptosis by *Drosophila* reaper, hid and grim through inhibition of IAP function" EMBO J 19(4):589-597 ( 2000).
Grether et al., "The head involution defective gene of *Drosophila melanogaster* functions in programmed cell death" Gene Dev 9:1694-1708 ( 1995).
Guo et al., "Ectopic Overexpression of Second Mitochondria-Derived Activator of Caspases (Smac/DIABLO) or Cotreatment with N-Terminus of Smac/DIABLO Peptide Potentiates Epothilone B Derivative-(BMS 247550) and Apo-2L/TRAIL-Induced Apoptosis" Blood 99:3419-3426 ( 2002).
Hinds et al., "Solution Structure of a Baculoviral Inhibitor of Apoptosis (IAP) Repeat" Nat Struct Biol 6(7):648-651 (Jul. 1999).
Hu et al., "Antisense oligonucleotides targeting XIAP induce apoptosis and enhance chemotherapeutic activity against human lung cancer cells in vitro and in vivo" Clin Cancer Res 9:2826-2836 ( 2003).
Internet Publication, "Maybridge Medchem, Bioisosteres in Medicinal Chemistry".
Jones et al., "Improved methods for building protein models in electron density maps and the location of errors in these models" Acta Cryst A47:110-119 ( 1991).
Keating et al. Proceedings of SPIE: In Vitro Diagnostic Instrument. Cohn, G.E. ed., vol. 3913:128-137 ( 2000).
Kipp et al., "Molecular Targeting of Inhibitor of Apoptosis Proteins Based on Small Molecule Mimics of Natural Binding Partners." Biochemistry 41:7344-7349 ( 2002).
Kolb et al., "Use of a novel homogeneous fluorescent technology in high throughput screening" J Biomol Screen 1(4):203-210 ( 1996).
LaCasse et al., "The inhibitors of apoptosis (IAPs) and their emerging role in cancer" Oncogene 17(25):3247-3259 ( 1998).
Lawton et al., "A Bioactive Modified Peptide, Aeruginosamide, Isolated from the Cyanbacterium *Microcystis aeruginosa*" J Org Chem 64:5329-5332 (Jun. 24, 1999).

(56) References Cited

OTHER PUBLICATIONS

Li, Lin et al., "A small molecule Smac mimic potentiates TRAIL- and TNF alpha-mediated cell death" Science 305:1471-1474 ( 2004).
Lin et al., "Resistance of bone marrow-derived macrophages to apoptosis is associated with the expression of X-linked inhibitor of apoptosis protein in primary cultures of bone marrow cells" Biochem J 353:299-306 ( 2001).
Liston et al., "Suppression of apoptosis in mammalian cells by NAIP and a related family of IAP genes" Nature 379:349-353 ( 1996).
Liu et al., "Eradication of Large Colon Tumor Xenografts by Targeted Delivery of Maytansinoids." P Natl Acad Sci USA 93:8618-8623 ( 1996).
Liu et al., "Structural Basis for Binding of Smac/DIABLO to the XIAP BIR3 Domain" Nature 408:1004-1008 (Dec. 2000).
Masuda et al., "Studies on mesoionic compounds. Part 11. Alkylation of 5-acylamino-1,2,3-thiadiazoles" J Chem Soc Perkin Trans 1 5:1591-1595 ( 1981).
Murshudov et al., "Refinement of Macromolecular Structures by the Maximum-Likelihood Method" Acta Cryst D53:240-255 ( 1997).
Ng and Bonavida, "X-Linked Inhibition of Apoptosis (XIAP) Blocks Apo2 Ligand/Tumor Necrosis Factor-Related Apoptosis-Inducing Ligand-Mediated Apoptosis of Prostate Cancer Cells in the Presence of . . . " Mol Cancer Ther 1:1051-1058 ( 2002).
Pan et al., "An Antagonist Decoy Receptor and a Death Domain-Containing Receptor for TRAIL" Science 277:815-818 (Aug. 1997).
Perrakis et al., "ARP/wARP and molecular replacement" Acta Crystallogr D57:1445-1450 ( 2001).
Pichon-Pesme et al., "On Building a Data Bank of Transferable Experimental Electron Density Parameters: Application to Polypeptides" J Phys Chem 99:6242-6250 ( 1995).
Prochiantz, A., "Getting Hydrophilic Compounds into Cells: Lessons from Homeopeptides" Curr Opin Neurobiol 6(5):629-634 ( 1996).
Riedl et al., "Structural Basis for the Inhibition of Caspase-3 by XIAP" Cell 104:791-800 (Mar. 9, 2001).
Salvesen and Nagase Proteolytic enzymes: A practical approach R.J. Beynon and J.S. Bond,Oxford, IRL Press,:83-104 ( 1989).
Sanna et al., "IAP suppression of apoptosis involves distinct mechanisms: the TAK1/JNK1 signaling cascade and caspase inhibition" Mol Cell Biol 22(6):1754-1766 (Mar. 2002).
Sasaki et al., "Down-regulation of X-linked inhibitor of apoptosis protein induces apoptosis in chemoresistant human ovarian cancer cells" Cancer Res 60(20):5659-5666 (Oct. 15, 2000).
Shiozaki et al., "Mechanism of XIAP-Mediated Inhibition of Caspase-9" Mol Cell 11:519-527 ( 2003).
Shuker et al., "Discovering High-Affinity Ligands for Proteins: SAR by NMR" Science 274:1531-1534 (Nov. 1996).
Sidhu et al., "Phage Display for Selection of Novel Binding Peptides" Method Enzymol 328:333-363 ( 2000).
Srinivasula et al., "A conserved XIAP-interaction motif in caspase-9 and Smac/DIABLO regulates caspase activity and apoptosis" Nature 410:112-116 ( 2001).
Srinivasula et al., "sickle, a Novel *Drosophila* Death Gene in the reaper/hid/grim Region, Encodes an IAP-Inhibitory Protein" Curr Biol 12:125-130 (Jan. 22, 2002).
Sun et al., "NMR Structure and Mutagenesis of the Inhibitor-of-Apoptosis Protein XIAP" Nature 401:818-822 (Oct. 1999).
Sun et al., "NMR Structure and Mutagenesis of the Third Bir Domain of the Inhibitor of Apoptosis Protein XIAP" J Biol Chem 275(43):33777-33781 (Oct. 27, 2000).
Takahashi et al., "A Single BIR Domain of XIAP Sufficient for Inhibiting Caspases" J Biol Chem 273(14):7787-7790 (Apr. 3, 1998).
Tamm et al., "Expression and prognostic significance of IAP-family genes in human cancers and myeloid leukemias" Clin Cancer Res 6(5):1796-1803 ( 2000).
Tenev et al., "Jafrac2 is an IAP antagonist that promotes cell death by liberating Dronc from DIAP1" EMBO J 21(19):5118-5129 ( 2002).
Thompson et al., "Design of potent and selective human cathepsin K inhibitors that span the active site" P Natl Acad Sci USA 94:14249-14254 (Dec. 1997).

Thompson et al., "Rational Design, Synthesis, and Crystallographic Analysis of a Hydroxyethylene-Based HIV-1 Protease Inhibitor Containing a Heterocyclic P1-P2 Amide Bond Isostere" J Med Chem 37:3100-3107 ( 1994).
Thompson et al., "Synthesis and Antiviral Activity of a Novel Class of HIV-1 Protease Inhibitors Containing a Heterocyclic P1-P2 Amide Bond Isostere" Bioorg Med Chem Lett 4(20):2241-2246 ( 1994).
Thompson, "Apoptosis in the Pathogenesis and Treatment of Disease" Science 267:1456-1462 ( 1995).
Vippagunta et al., "Crystalline solids" Adv Drug Deliver Rev 48:3-26 ( 2001).
Vucic D et al. et al., "Engineering ML-IAP to produce an extraordinarily potent caspase 9 inhibitor: implications for Smac-dependent anti-apoptotic activity of ML-IAP" Biochem J 385(Part 1):11-20 (Jan. 2005).
Vucic et al., "ML-IAP, A Novel Inhibitor of Apoptosis that is Preferentially Expressed in Human Melanomas" Current Bio 10:1359-1366 ( 2000).
Vucic et al., "SMAC Negatively Regulates the Anti-apoptotic Activity of Melanoma Inhibitor of Apoptosis (ML-IAP)" J Biol Chem 277(14):12275-12279 (Apr. 5, 2002).
White et al. et al., "Genetic Control of Programmed Cell Death in *Drosophila*" Science 264:677-683 ( 1994).
Wing et al. et al., "*Drosophila* sickle Is a Novel grim-reaper Cell Death Activator" Curr Biol 12:131-135 ( 2002).
Wu et al., "Structural Analysis of a Functional DIAP1 Fragment Bound to Grim and Hid Peptides" Mol Cell 8:95-104 (Jul. 2001).
Wu et al., "Structural Basis of IAP Recognition by Smac/DIABLO" Nature 408:1008-1012 (Dec. 2000).
Yang et al., "Predominant suppression of apoptosome by inhibitor of apoptosis protein in non-small cell lung cancer H460 cells: therapeutic effect of a novel polyarginine-conjugated smac peptide" Cancer Res 63:831-837 (Feb. 15, 2003).
Yokokawa et al., "Total synthesis and conformational studies of ceratospongamide, a bioactive cyclic heptapeptide from marine origin" Tetrahedron 505:8127-8143 (Apr. 18, 2002).
Yokokawa et al., "Total Synthesis of cis,cis-Ceratospongamide, a Bioactive Thiazole-Containing Cyclic Peptide from Marine Origin" Synlett:986-988 ( 2001).
Boden, C.D.J. et al. (Dec. 9, 1996). "Total Synthesis of the Thiazoline-Based Cyclopeptide Cyclodidemnamide," *Tetrahedron Letters* 37(50):9111-9114.
Chari, R.V.J. et al. (Jan. 1, 1992). "Immunoconjugates Containing Novel Maytansinoids: Promising Anticancer Drugs," *Cancer Research* 52:127-131.
Extended European Search Report mailed Dec. 28, 2010, for EP Application No. 08747109.0, filed on Apr. 29, 2008, nine pages.
Fojo, T. et al. (2003). "Strategies for Reversing Drug Resistance," *Oncogene* 22:7512-7523.
Freshney, R.I. (1983). *Culture of Animal Cells, A Manual of Basic Technique*, Alan R. Liss, Inc., New York, New York, p. 4.
Giménez-Bonafé, P. et al. (2009). "Overcoming Drug Resistance by Enhacing Apoptosis of Tumor Cells," *Current Cancer Drug Targets* 9:320-340.
Hamada, Y. et al. (1985). "New Methods and Reagents in Organic Synthesis. 56. Total Syntheses of Patellamides B and C, Cytotoxic Cyclic Peptides From a Tunicate 2. Their Real Structures Have Been Determined by Their Syntheses," *Tetrahedron Letters* 26(42):5159-5162.
Holder, J.R. et al. (Dec. 19, 2002, e-pub. Nov. 23, 2002). "Structure-Activity Relationships of the Melanocortin Tetrapeptide Ac-His-D-Phe-Arg-Trp-$NH_2$ at the Mouse Melanocortin Receptors 4. Modifications at the Trp Position" *J Med. Chem., American Chem. Society* 45(26):5736-5744.
International Search Report and Written Opinion mailed on May 7, 2009, for PCT Patent Application No. PCT/US2009/030674, filed on Jan. 9, 2009, twenty-one pages.
Ireland, C.M. et al. (1982). "Antineoplastic Cyclic Peptides From the Marine Tunicate *Lissoclinum patella*" *J. Org. Chem.* 47:1807-1811.
Joyeau, R. et al. (2000). "Synthesis and Activity of Pyrrolidinyl- and Thiazolidinyl-Dipeptide Derivatives as Inhibitors of the Tc80 Prolyl Oligopeptidase From *Trypanosoma cruzi*," *Eur. J. Med Chem* 35(2):257-266.

(56) References Cited

OTHER PUBLICATIONS

Moody, C.J. et al. (1999, e-pub. Oct. 23, 1999). "Synthesis of Virenamide B, a Cytotoxic Thiazole-Containing Peptide," *Organic Chem.* 64:8715-8717.

Murray, E.D. et al. (Sep. 10, 1984). "Synthetic Peptide Substrates for the Erythrocyte Protein Carboxyl Methyltransferase," *J Biol. Chem.* 259(17):10722-10732.

Norley, M.C. et al. (1998). "Total Synthesis and Revision of Stereochemistry of Cyclodidemnamide, a Novel Cyclopeptide From the Marine Ascidian *Didemnum molle,*" *Tetrahedron Letters* 39:3087-3090.

Ösz, K. et al. (Apr. 23, 2003). "Transition Metal Complexes of Bis(imidazol-2-yl) Derivatives of Dipeptides," *Dalton Transactions* pp. 2009-2016.

Schimmer, A.D. et al. (2005). "Targeting the IAP Family of Caspase Inhibitors as an Emerging Therapeutic Strategy," *Hematology* pp. 215-219.

STN International. (Apr. 15, 2009). "STN-11739030A," last visited on Sep. 15, 2009, thirty-seven pages.

Stark, G.R. (May 1, 1968). "Sequential Degradation of Peptides From Their Carboxyl Termini With Ammonium Thiocyanate and Acetic Anhydride," *Biochemistry* 7(5):1796-1807.

Supplementary European Search Report dated Sep. 2, 2010, received in corresponding EP Application No. 06850324.2, six pages.

U.S. Appl. No. 60/560,186, filed Apr. 7, 2004, seventy-four pages.

West, A.R. (1984). "Solid Solutions," Chapter 10 in *Solid State Chemistry and Its Applications*, John Wiley and Sons, Chichester, England, pp. 358 and 365.

Supplementary EP Search Report dated Sep. 23, 2011, in corresponding EP Application No. 09805348.1.9.

Ndubaku, Chudi et al., "Antagonism of c-IAP and XIAP Proteins Is Required for Efficient Induction of Cell Death by Small-Molecule IAP Antagonists" ACS Chemical Biology 4(7):557-566 (Jul. 17, 2009).

Anonymous. *Compendium of Chemical Terminology Gold Book*, Version 2.3 edition, International Union of Pure and Applied Chemistry, 4 pages (title page plus pp. 57, 212, and 1052) (Oct. 11, 2011).

Attachment to Communication Letter to the European Patent Office from Jan Robert Naefe, Grafelfing, Germany, mailed Aug. 16, 2012, for European Patent Application No. 05854815.7, "Representation of Non-Exemplified Groups Q," one page.

Ciufolini et al., "Studies Toward Thiostrepton Antibiotics: Assembly of the Central Pyridine-Thiazole Cluster of Mircrococcins," *J. Org. Chem.* 62:3804-3805 ( 1997).

Communication Letter to the European Patent Office from Jan Robert Naefe, Grafelfing, Germany, mailed Aug. 16, 2012, for European Patent Application No. 05854815.7, 21 pages.

Communication of Further Opposition mailed Jun. 16, 2011, for European Patent Application No. 05854815.7, filed on Dec. 19, 2005, two pages.

Hamada et al., "New methods and reagents in organic synthesis. 58. A synthesis of patellamide A, a cytotoxic cyclic peptide from a tunicate. Revision of its proposed structure," *Tetrahedron Letters* 26(52):6501-6504 (1985).

Nakamura et al. "Stereochemistry and Total Synthesis of Dolastatin E," *Tetrahedron Letters* 36(28):5059-5062 (1995).

Response to Notice of Opposition mailed on Dec. 22, 2011, for European Patent Application No. 05854815.7, filed on Dec. 19, 2005, 19 pages (Dec. 22, 2011).

SciFinder® Search Result, "Explore Reactions by Substructure (ID 4)," one page (SciFinder® Aug. 8, 2012).

SciFinder® Search Result, "Explore Reactions by Substructure (ID 6)," one page. (SciFinder® Aug. 8, 2012).

Bajaj, K. et al. (Dec. 2007). "Stereochemical Criteria for Prediction of the Effects of Proline Mutations on Protein Stability," *PLoS Computational Biology* 3(12)(e241):2465-2475.

MacArthur, M.W. et al. (Mar. 20, 1991). "Influence of Proline Residues on Protein Conformation," *J. Mol. Biol.* 218(2):397-412.

\* cited by examiner

SEQUENCE LISTING

<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

```
Met Gly Ser Ser His His His His His His Ser Ser Gly Leu Val
 1               5                   10                  15

Pro Arg Gly Ser His Met Leu Glu Thr Glu Glu Glu Glu Glu Glu
                20                  25                  30

Gly Ala Gly Ala Thr Leu Ser Arg Gly Pro Ala Phe Pro Gly Met
                35                  40                  45

Gly Ser Glu Glu Leu Arg Leu Ala Ser Phe Tyr Asp Trp Pro Leu
                50                  55                  60

Thr Ala Glu Val Pro Pro Glu Leu Leu Ala Ala Ala Gly Phe Phe
                65                  70                  75

His Thr Gly His Gln Asp Lys Val Arg Cys Phe Phe Cys Tyr Gly
                80                  85                  90

Gly Leu Gln Ser Trp Lys Arg Gly Asp Asp Pro Trp Thr Glu His
                95                  100                 105

Ala Lys Trp Phe Pro Gly Cys Gln Phe Leu Leu Arg Ser Lys Gly
                110                 115                 120

Gln Glu Tyr Ile Asn Asn Ile His Leu Thr His Ser Leu
                125                 130
```

INHIBITORS OF IAP

PRIORITY CLAIM

This application claims priority to U.S. provisional application No. 61/085,844 filed on 2 Aug. 2008, the contents of which are incorporated herein by reference.

FIELD OF THE INVENTION

The present invention relates to organic compounds useful for therapy and/or prophylaxis in a mammal, and in particular to inhibitors of IAP proteins useful for treating cancers.

BACKGROUND OF THE INVENTION

Apoptosis or programmed cell death is a genetically and biochemically regulated mechanism that plays an important role in development and homeostasis in invertebrates as well as vertebrates. Aberrancies in apoptosis that lead to premature cell death have been linked to a variety of developmental disorders. Deficiencies in apoptosis that result in the lack of cell death have been linked to cancer and chronic viral infections (Thompson et al., (1995) Science 267, 1456-1462).

One of the key effector molecules in apoptosis are the caspases (cysteine containing aspartate specific proteases). Caspases are strong proteases, cleaving after aspartic acid residues and once activated, digest vital cell proteins from within the cell. Since caspases are such strong proteases, tight control of this family of proteins is necessary to prevent premature cell death. In general, caspases are synthesized as largely inactive zymogens that require proteolytic processing in order to be active. This proteolytic processing is only one of the ways in which caspases are regulated. The second mechanism is through a family of proteins that bind and inhibit caspases.

A family of molecules that inhibit caspases are the Inhibitors of Apoptosis (IAP) (Deveraux et al., J Clin Immunol (1999), 19:388-398). IAPs were originally discovered in baculovirus by their functional ability to substitute for P35 protein, an anti-apoptotic gene (Crook et al. (1993) J Virology 67, 2168-2174). IAPs have been described in organisms ranging from Drosophila to human. Regardless of their origin, structurally, IAPs comprise one to three Baculovirus IAP repeat (BIR) domains, and most of them also possess a carboxyl-terminal RING finger motif The BIR domain itself is a zinc binding domain of about 70 residues comprising 4 alpha-helices and 3 beta strands, with cysteine and histidine residues that coordinate the zinc ion (Hinds et al., (1999) Nat. Struct. Biol. 6, 648-651). It is the BIR domain that is believed to cause the anti-apoptotic effect by inhibiting the caspases and thus inhibiting apoptosis. As an example, human X-chromosome linked IAP (XIAP) inhibits caspase 3, caspase 7 and the Apaf-1-cytochrome C mediated activation of caspase 9 (Deveraux et al., (1998) EMBO J. 17, 2215-2223). Caspases 3 and 7 are inhibited by the BIR2 domain of XIAP, while the BIR3 domain of XIAP is responsible for the inhibition of caspase 9 activity. XIAP is expressed ubiquitously in most adult and fetal tissues (Liston et al, Nature, 1996, 379(6563): 349), and is overexpressed in a number of tumor cell lines of the NCI 60 cell line panel (Fong et al, Genomics, 2000, 70:113; Tamm et al, Clin. Cancer Res. 2000, 6(5):1796). Overexpression of XIAP in tumor cells has been demonstrated to confer protection against a variety of pro-apoptotic stimuli and promotes resistance to chemotherapy (LaCasse et al, Oncogene, 1998, 17(25):3247). Consistent with this, a strong correlation between XIAP protein levels and survival has been demonstrated for patients with acute myelogenous leukemia (Tamm et al, supra). Down-regulation of XIAP expression by antisense oligonucleotides has been shown to sensitize tumor cells to death induced by a wide range of pro-apoptotic agents, both in vitro and in vivo (Sasaki et al, Cancer Res., 2000, 60(20):5659; Lin et al, Biochem J., 2001, 353:299; Hu et al, Clin. Cancer Res., 2003, 9(7):2826). Smac/DIABLO-derived peptides have also been demonstrated to sensitize a number of different tumor cell lines to apoptosis induced by a variety of pro-apoptotic drugs (Arnt et al, J. Biol. Chem., 2002, 277(46):44236; Fulda et al, Nature Med., 2002, 8(8):808; Guo et al, Blood, 2002, 99(9):3419; Vucic et al, J. Biol. Chem., 2002, 277(14):12275; Yang et al, Cancer Res., 2003, 63(4):831).

Melanoma IAP (ML-IAP) is an IAP not detectable in most normal adult tissues but is strongly upregulated in melanoma (Vucic et al., (2000) Current Bio 10:1359-1366). Determination of protein structure demonstrated significant homology of the ML-IAP BIR and RING finger domains to corresponding domains present in human XIAP, C-IAP1 and C-IAP2. The BIR domain of ML-IAP appears to have the most similarities to the BIR2 and BIR3 of XIAP, C-IAP1 and C-IAP2, and appears to be responsible for the inhibition of apoptosis, as determined by deletional analysis. Furthermore, Vucic et al., demonstrated that ML-IAP could inhibit chemotherapeutic agent induced apoptosis. Agents such as adriamycin and 4-tertiary butylphenol (4-TBP) were tested in a cell culture system of melanomas overexpressing ML-IAP and the chemotherapeutic agents were significantly less effective in killing the cells when compared to a normal melanocyte control. The mechanism by which ML-IAP produces an anti-apoptotic activity is in part through inhibition of caspase 3 and 9. ML-IAP did not effectively inhibit caspases 1, 2, 6, or 8.

Since apoptosis is a strictly controlled pathway with multiple interacting factors, the discovery that IAPs themselves are regulated was not unusual. In the fruit fly Drosophila, the Reaper (rpr), Head Involution Defective (hid) and GRIM proteins physically interact with and inhibit the anti-apoptotic activity of the Drosophila family of IAPs. In the mammal, the proteins SMAC/DIABLO act to block the IAPs and allow apoptosis to proceed. It was shown that during normal apoptosis, SMAC is processed into an active form and is released from the mitochondria into the cytoplasm where it physically binds to IAPs and prevents the IAP from binding to a caspase. This inhibition of the IAP allows the caspase to remain active and thus proceed with apoptosis. Interestingly, sequence homology between the IAP inhibitors shows that there is a four amino acid motif in the N-terminus of the processed, active proteins. This tetrapeptide appears to bind into a hydrophobic pocket in the BIR domain and disrupts the BIR domain binding to caspases (Chai et al., (2000) Nature 406: 855-862, Liu et al., (2000) Nature 408:1004-1008, Wu et al., (2000) Nature 408 1008-1012).

SUMMARY OF THE INVENTION

In one aspect of the present invention there is provided novel inhibitors of IAP proteins having the general formula (I)

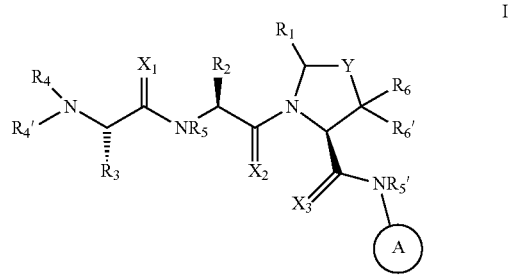

wherein $X_1$, $X_2$ and $X_3$ are independently O or S;

Y is $(CHR_7)_n$, O or S; wherein n is 1 or 2 and $R_7$ is H, halogen, alkyl, aryl, aralkyl, amino, arylamino, alkylamino, aralkylamino, alkoxy, aryloxy or aralkyloxy;

A is a 6-member aromatic ring or a heteroaromatic ring comprising 1 to 4 heteroatoms optionally substituted with amino, hydroxyl, mercapto, halogen, carboxyl, amidino, guanidino, alkyl, alkoxy, aryl, aryloxy, acyl, acyloxy, acylamino, alkoxycarbonylamino, cycloalkyl, alkylthio, alkylsulfinyl, alkylsulfonyl, aminosulfonyl, alkylaminosulfonyl, alkylsulfonylamino or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, alkoxy, haloalkyl, amino, nitro, cyano, cycloalkyl, aryl or a heterocycle $R_1$ is H or $R_1$ and $R_2$ together form a 5-8 member ring;

$R_2$ is alkyl cycloalkyl, cycloalkyl-alkyl, aryl, aralkyl, a heterocycle or heterocycloalkyl; each optionally substituted with hydroxyl, mercapto, halogen, amino, carboxyl, alkyl, haloalkyl, alkoxy or alkylthio;

$R_3$ is H or alkyl;

$R_4$ and $R_4'$ are independently H, hydroxyl, amino, alkyl, aryl, aralkyl, cycloalkyl, cycloalkyl-alkyl, heteroaryl, or heteroarylalkyl, wherein each alkyl, aryl, aralkyl, cycloalkyl, cycloalkyl-alkyl, heteroaryl and heteroarylalkyl is optionally substituted with halogen, hydroxyl, mercapto, carboxyl, alkyl, alkoxy, amino or nitro;

$R_5$, and $R_5'$ are each independently H or alkyl;

$R_6$, and $R_6'$ are each independently H, alkyl, aryl or aralkyl;

and salts and solvates thereof.

In another aspect of the invention, there are provided compositions comprising compounds of formula I and a carrier, diluent or excipient.

In another aspect of the invention, there is provided a method of inducing apoptosis in a cell comprising introducing into said cell a compound of formula I.

In another aspect of the invention, there is provided a method of sensitizing a cell to an apoptotic signal comprising introducing into said cell a compound of formula I.

In another aspect of the invention, there is provided a method for inhibiting the binding of an IAP protein to a caspase protein comprising contacting said IAP protein with a compound of formula I.

In another aspect of the invention, there is provided a method for treating a disease or condition associated with the overexpression of an IAP protein in a mammal, comprising administering to said mammal an effective amount of a compound of formula I.

DETAILED DESCRIPTION OF THE PREFERRED EMBODIMENTS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Alkyl" means a branched or unbranched, saturated or unsaturated (i.e. alkenyl, alkynyl) aliphatic hydrocarbon group, having up to 12 carbon atoms unless otherwise specified. When used as part of another term, for example "alkylamino", the alkyl portion is preferably a saturated hydrocarbon chain, however also includes unsaturated hydrocarbon carbon chains such as "alkenylamino" and "alkynylamino. Examples of preferred alkyl groups include methyl, ethyl, n-propyl, isopropyl, n-butyl, iso-butyl, sec-butyl, tert-butyl, n-pentyl, 2-methylbutyl, 2,2-dimethylpropyl, n-hexyl, 2-methylpentyl, 2,2-dimethylbutyl, n-heptyl, 3-heptyl, 2-methylhexyl, and the like. The terms "lower alkyl" "$C_1$-$C_4$ alkyl" and "alkyl of 1 to 4 carbon atoms" are synonymous and used interchangeably to mean methyl, ethyl, 1-propyl, isopropyl, cyclopropyl, 1-butyl, sec-butyl or t-butyl. Unless specified, substituted, alkyl groups may contain one (preferably), two, three or four substituents which may be the same or different. Examples of the above substituted alkyl groups include, but are not limited to; cyanomethyl, nitromethyl, hydroxymethyl, trityloxymethyl, propionyloxymethyl, aminomethyl, carboxymethyl, carboxyethyl, carboxypropyl, alkyloxycarbonylmethyl, allyloxycarbonylaminomethyl, carbamoyloxymethyl, methoxymethyl, ethoxymethyl, t-butoxymethyl, acetoxymethyl, chloromethyl, bromomethyl, iodomethyl, trifluoromethyl, 6-hydroxyhexyl, 2,4-dichloro(n-butyl), 2-amino(iso-propyl), 2-carbamoyloxyethyl and the like. The alkyl group may also be substituted with a carbocycle group. Examples include cyclopropylmethyl, cyclobutylmethyl, cyclopentylmethyl, and cyclohexylmethyl groups, as well as the corresponding -ethyl, -propyl, -butyl, -pentyl, -hexyl groups, etc. Preferred substituted alkyls are substituted methyls e.g. a methyl group substituted by the same substituents as the "substituted $C_n$-$C_m$ alkyl" group. Examples of the substituted methyl group include groups such as hydroxymethyl, protected hydroxymethyl (e.g. tetrahydropyranyloxymethyl), acetoxymethyl, carbamoyloxymethyl, trifluoromethyl, chloromethyl, carboxymethyl, bromomethyl and iodomethyl.

"Amidine" means the group —C(NH)—NHR in which R is H, alkyl, a carbocycle, a heterocycle, carbocycle-substituted alkyl or heterocycle-substituted alkyl wherein the alkyl, alkoxy, carbocycle and heterocycle are as defined herein. A particular amidine is the group —NH—C(NH)—$NH_2$.

"Amino" means primary (i.e. —$NH_2$), secondary (i.e. —NRH) and tertiary (i.e. —NRR) amines in which R is H, alkyl, a carbocycle, a heterocycle, carbocycle-substituted alkyl or heterocycle-substituted alkyl wherein the alkyl, alkoxy, carbocycle and heterocycle are as defined herein. Particular secondary and tertiary amines are alkylamine, dialkylamine, arylamine, diarylamine, aralkylamine and diaralkylamine wherein the alkyl is as herein defined and optionally substituted. Particular secondary and tertiary amines are methylamine, ethylamine, propylamine, isopropylamine, phenylamine, benzylamine dimethylamine, diethylamine, dipropylamine and disopropylamine.

"Amino-protecting group" as used herein refers to a derivative of the groups commonly employed to block or protect an amino group while reactions are carried out on other functional groups on the compound. Examples of such protecting groups include carbamates, amides, alkyl and aryl groups, imines, as well as many N-heteroatom derivatives which can be removed to regenerate the desired amine group. Particular amino protecting groups are Boc, Fmoc and Cbz. Further examples of these groups are found in T. W. Greene and P. G. M. Wuts, "Protective Groups in Organic Synthesis", $2^{nd}$ ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino" refers to an amino group substituted with one of the above amino-protecting groups.

"Aryl" when used alone or as part of another term means a carbocyclic aromatic group whether or not fused having the number of carbon atoms designated or if no number is designated, up to 14 carbon atoms. Particular aryl groups are phenyl, naphthyl, biphenyl, phenanthrenyl, naphthacenyl, and the like (see e.g. *Lang's Handbook of Chemistry* (Dean, J. A., ed) 13$^{th}$ ed. Table 7-2 [1985]). A particular aryl is phenyl. Substituted phenyl or substituted aryl means a phenyl group or aryl group substituted with one, two, three, four or five, for example 1-2, 1-3 or 1-4 substituents chosen, unless otherwise specified, from halogen (F, Cl, Br, I), hydroxy, protected hydroxy, cyano, nitro, alkyl (for example $C_1$-$C_6$ alkyl), alkoxy (for example $C_1$-$C_6$ alkoxy), benzyloxy, carboxy, protected carboxy, carboxymethyl, protected carboxymethyl, hydroxymethyl, protected hydroxymethyl, aminomethyl, protected aminomethyl, trifluoromethyl, alkylsulfonylamino, alkylsulfonylaminoalkyl, arylsulfonylamino, arylsulonylaminoalkyl, heterocyclylsulfonylamino, heterocyclylsulfonylaminoalkyl, heterocyclyl, aryl, or other groups specified. One or more methyne (CH) and/or methylene ($CH_2$) groups in these substituents may in turn be substituted with a similar group as those denoted above. Examples of the term "substituted phenyl" includes but is not limited to a mono- or di(halo) phenyl group such as 2-chlorophenyl, 2-bromophenyl, 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono- or di(hydroxy)phenyl group such as 4-hydroxyphenyl, 3-hydroxyphenyl, 2,4-dihydroxyphenyl, the protected-hydroxy derivatives thereof and the like; a nitrophenyl group such as 3- or 4-nitrophenyl; a cyanophenyl group, for example, 4-cyanophenyl; a mono- or di(lower alkyl)phenyl group such as 4-methylphenyl, 2,4-dimethylphenyl, 2-methylphenyl, 4-(iso-propyl)phenyl, 4-ethylphenyl, 3-(n-propyl)phenyl and the like; a mono or di(alkoxy)phenyl group, for example, 3,4-dimethoxyphenyl, 3-methoxy-4-benzyloxyphenyl, 3-methoxy-4-(1-chloromethyl)benzyloxy-phenyl, 3-ethoxyphenyl, 4-(isopropoxy) phenyl, 4-(t-butoxy)phenyl, 3-ethoxy-4-methoxyphenyl and the like; 3- or 4-trifluoromethylphenyl; a mono- or dicarboxyphenyl or (protected carboxy)phenyl group such 4-carboxyphenyl; a mono- or di(hydroxymethyl)phenyl or (protected hydroxymethyl)phenyl such as 3-(protected hydroxymethyl) phenyl or 3,4-di(hydroxymethyl)phenyl; a mono- or di(aminomethyl)phenyl or (protected aminomethyl)phenyl such as 2-(aminomethyl)phenyl or 2,4-(protected aminomethyl)phenyl; or a mono- or di(N-(methylsulfonylamino))phenyl such as 3-(N-methylsulfonylamino))phenyl. Also, the term "substituted phenyl" represents disubstituted phenyl groups where the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like, as well as trisubstituted phenyl groups where the substituents are different, for example 3-methoxy-4-benzyloxy-6-methyl sulfonylamino, 3-methoxy-4-benzyloxy-6-phenyl sulfonylamino, and tetrasubstituted phenyl groups where the substituents are different such as 3-methoxy-4-benzyloxy-5-methyl-6-phenyl sulfonylamino Particular substituted phenyl groups include the 2-chlorophenyl, 2-aminophenyl, 2-bromophenyl, 3-methoxyphenyl, 3-ethoxy-phenyl, 4-benzyloxyphenyl, 4-methoxyphenyl, 3-ethoxy-4-benzyloxyphenyl, 3,4-diethoxyphenyl, 3-methoxy-4-benzyloxyphenyl, 3-methoxy-4-(1-chloromethyl)benzyloxy-phenyl, 3-methoxy-4-(1-chloromethyl)benzyloxy-6-methyl sulfonyl aminophenyl groups. Fused aryl rings may also be substituted with any, for example 1, 2 or 3, of the substituents specified herein in the same manner as substituted alkyl groups.

"Carbocyclyl", "carbocyclylic", "carbocycle" and "carbocyclo" alone and when used as a moiety in a complex group such as a carbocycloalkyl group, refers to a mono-, bi-, or tricyclic aliphatic ring having 3 to 14 carbon atoms, for example 3 to 7 carbon atoms, which may be saturated or unsaturated, aromatic or non-aromatic. Particular saturated carbocyclic groups are cyclopropyl, cyclobutyl, cyclopentyl and cyclohexyl groups. A particular saturated carbocycle is cyclopropyl. Another particular saturated carbocycle is cyclohexyl. Particular unsaturated carbocycles are aromatic e.g. aryl groups as previously defined, for example phenyl. The terms "substituted carbocyclyl", "carbocycle" and "carbocyclo" mean these groups substituted by the same substituents as the "substituted alkyl" group.

"Carboxy-protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, alkyl such as t-butyl or t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivatized carboxylic acid is stable to the condition of subsequent reaction(s) on other positions of the molecule and can be removed at the appropriate point without disrupting the remainder of the molecule. In particular, it is important not to subject a carboxy-protected molecule to strong nucleophilic bases, such as lithium hydroxide or NaOH, or reductive conditions employing highly activated metal hydrides such as $LiAlH_4$. (Such harsh removal conditions are also to be avoided when removing amino-protecting groups and hydroxy-protecting groups, discussed below.) Particular carboxylic acid protecting groups are the alkyl (e.g. methyl, ethyl, t-butyl), allyl, benzyl and p-nitrobenzyl groups. Similar carboxy-protecting groups used in the cephalosporin, penicillin and peptide arts can also be used to protect a carboxy group substituents. Further examples of these groups are found in T. W. Greene and P. G. M. Wuts, "Protective Groups in Organic Synthesis", 2$^{nd}$ ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy" refers to a carboxy group substituted with one of the above carboxy-protecting groups. "Guanidine" means the group —NH—C(NH)—NHR in which R is H, alkyl, a carbocycle, a heterocycle, carbocycle-substituted alkyl or heterocycle-substituted alkyl wherein the alkyl, alkoxy, carbocycle and heterocycle are as defined herein. A particular guanidine is the group —NH—C(NH)—$NH_2$.

"Hydroxy-protecting group" as used herein refers to a derivative of the hydroxy group commonly employed to block or protect the hydroxy group while reactions are carried out on other functional groups on the compound. Examples of such protecting groups include tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", $2^{nd}$ ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy" refers to a hydroxy group substituted with one of the above hydroxy-protecting groups.

"Heterocyclic group", "heterocyclic", "heterocycle", "heterocyclyl", or "heterocyclo" alone and when used as a moiety in a complex group such as a heterocycloalkyl group, are used interchangeably and refer to any mono-, bi-, or tricyclic, saturated or unsaturated, aromatic (heteroaryl) or non-aromatic ring having the number of atoms designated, generally from 5 to about 14 ring atoms, where the ring atoms are carbon and at least one heteroatom (nitrogen, sulfur or oxygen), for example 1 to 4 heteroatoms. Typically, a 5-membered ring has 0 to 2 double bonds and 6- or 7-membered ring has 0 to 3 double bonds and the nitrogen or sulfur heteroatoms may optionally be oxidized (e.g. SO, $SO_2$), and any nitrogen heteroatom may optionally be quaternized. Particular non-aromatic heterocycles are morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. A "heterocycloalkyl" group is a heterocycle group as defined above covalently bonded to an alkyl group as defined above. Particular 5-membered heterocycles containing a sulfur or oxygen atom and one to three nitrogen atoms are thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Particular 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a particular group. Substituents for "optionally substituted heterocycles", and further examples of the 5- and 6-membered ring systems discussed above can be found in W. Druckheimer et al., U.S. Pat. No. 4,278,793. In a particular embodiment, such optionally substituted heterocycle groups are substituted with hydroxyl, alkyl, alkoxy, acyl, halogen, mercapto, oxo, carboxyl, acyl, halo-substituted alkyl, amino, cyano, nitro, amidino and guanidino.

"Heteroaryl" alone and when used as a moiety in a complex group such as a heteroaralkyl group, refers to any mono-, bi-, or tricyclic aromatic ring system having the number of atoms designated where at least one ring is a 5-, 6- or 7-membered ring containing from one to four heteroatoms selected from the group nitrogen, oxygen, and sulfur, and in a particular embodiment at least one heteroatom is nitrogen (*Lang's Handbook of Chemistry*, supra). Included in the definition are any bicyclic groups where any of the above heteroaryl rings are fused to a benzene ring. Particular heteroaryls incorporate a nitrogen or oxygen heteroatom. The following ring systems are examples of the heteroaryl (whether substituted or unsubstituted) groups denoted by the term "heteroaryl": thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo[1,5-b]pyridazinyl and purinyl, as well as benzo-fused derivatives, for example benzoxazolyl, benzofuryl, benzothiazolyl, benzothiadiazolyl, benzotriazolyl, benzoimidazolyl and indolyl. A particular "heteroaryl" is: 1,3-thiazol-2-yl, 4-(carboxymethyl)-5-methyl-1,3-thiazol-2-yl, 4-(carboxymethyl)-5-methyl-1,3-thiazol-2-yl sodium salt, 1,2,4-thiadiazol-5-yl, 3-methyl-1,2,4-thiadiazol-5-yl, 1,3,4-triazol-5-yl, 2-methyl-1,3,4-triazol-5-yl, 2-hydroxy-1,3,4-triazol-5-yl, 2-carboxy-4-methyl-1,3,4-triazol-5-yl sodium salt, 2-carb oxy-4-methyl-1,3,4-triazol-5-yl, 1,3-oxazol-2-yl, 1,3,4-oxadiazol-5-yl, 2-methyl-1,3,4-oxadiazol-5-yl, 2-(hydroxymethyl)-1,3,4-oxadiazol-5-yl, 1,2,4-oxadiazol-5-yl, 1,3,4-thiadiazol-5-yl, 2-thiol-1,3,4-thiadiazol-5-yl, 2-(methylthio)-1,3,4-thiadiazol-5-yl, 2-amino-1,3,4-thiadiazol-5-yl, 1H-tetrazol-5-yl, 1-methyl-1H-tetrazol-5-yl, 1-(1-(dimethylamino)eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 2-methyl-1H-tetrazol-5-yl, 1,2,3-triazol-5-yl, 1-methyl-1,2,3-triazol-5-yl, 2-methyl-1,2,3-triazol-5-yl, 4-methyl-1,2,3-triazol-5-yl, pyrid-2-yl N-oxide, 6-methoxy-2-(n-oxide)-pyridaz-3-yl, 6-hydroxypyridaz-3-yl, 1-methylpyrid-2-yl, 1-methylpyrid-4-yl, 2-hydroxypyrimid-4-yl, 1,4,5,6-tetrahydro-5,6-dioxo-4-methyl-as-triazin-3-yl, 1,4,5,6-tetrahydro-4-(formylmethyl)-5,6-dioxo-as-triazin-3-yl, 2,5-dihydro-5-oxo-6-hydroxy-astriazin-3-yl, 2,5-dihydro-5-oxo-6-hydroxy-as-triazin-3-yl sodium salt, 2,5-dihydro-5-oxo-6-hydroxy-2-methyl-astriazin-3-yl sodium salt, 2,5-dihydro-5-oxo-6-hydroxy-2-methyl-as-triazin-3-yl, 2,5-dihydro-5-oxo-6-methoxy-2-methyl-as-triazin-3-yl, 2,5-dihydro-5-oxo-as-triazin-3-yl, 2,5-dihydro-5-oxo-2-methyl-as-triazin-3-yl, 2,5-dihydro-5-oxo-2,6-dimethyl-as-triazin-3-yl, tetrazolo[1,5-b]pyridazin-6-yl and 8-aminotetrazolo[1,5-b]-pyridazin-6-yl. An alternative group of "heteroaryl" includes; 4-(carboxymethyl)-5-methyl-1,3-thiazol-2-yl, 4-(carboxymethyl)-5-methyl-1,3-thiazol-2-yl sodium salt, 1,3,4-triazol-5-yl, 2-methyl-1,3,4-triazol-5-yl, 1H-tetrazol-5-yl, 1-methyl-1H-tetrazol-5-yl, 1-(1-(dimethylamino) eth-2-yl)-1H-tetrazol-5-yl, 1-(carboxymethyl)-1H-tetrazol-5-yl, 1-(carboxymethyl)-1H-tetrazol-5-yl sodium salt, 1-(methylsulfonic acid)-1H-tetrazol-5-yl, 1-(methylsulfonic acid)-1H-tetrazol-5-yl sodium salt, 1,2,3-triazol-5-yl, 1,4,5,6-tetrahydro-5,6-dioxo-4-methyl-as-triazin-3-yl, 1,4,5, 6-tetrahydro-4-(2-formylmethyl)-5,6-dioxo-as-triazin-3-yl, 2,5-dihydro-5-oxo-6-hydroxy-2-methyl-as-triazin-3-yl sodium salt, 2,5-dihydro-5-oxo-6-hydroxy-2-methyl-as-triazin-3-yl, tetrazolo[1,5-b]pyridazin-6-yl, and 8-aminotetrazolo[1,5-b]pyridazin-6-yl. Heteroaryl groups are optionally substituted as described for heterocycles.

"Inhibitor" means a compound which reduces or prevents the binding of IAP proteins to caspase proteins or which reduces or prevents the inhibition of apoptosis by an IAP protein. Alternatively, "inhibitor" means a compound which prevents the binding interaction of CIAP-1, C-IAP-2, X-IAP with caspases or the binding interaction of ML-IAP with SMAC.

"Optionally substituted" unless otherwise specified means that a group may be unsubstituted or substituted by one or more (e.g. 0, 1, 2, 3 or 4) of the substituents listed for that group in which said substituents may be the same or different. In an embodiment an optionally substituted group has 1 substituent. In another embodiment an optionally substituted group has 2 substituents. In another embodiment an optionally substituted group has 3 substituents.

"Pharmaceutically acceptable salts" include both acid and base addition salts. "Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly organic non-toxic bases are isopropylamine, diethylamine, ethanolamine, trimethamine, dicyclohexylamine, choline, and caffeine.

"Sulfonyl" means a —$SO_2$—R group in which R is H, alkyl, a carbocycle, a heterocycle, carbocycle-substituted alkyl or heterocycle-substituted alkyl wherein the alkyl, alkoxy, carbocycle and heterocycle are as defined herein. Particular sulfonyl groups are alkylsulfonyl (i.e. —$SO_2$-alkyl), for example methylsulfonyl; arylsulfonyl, for example phenylsulfonyl; aralkylsulfonyl, for example benzylsulfonyl.

The phrase "or salts or solvates thereof" as used herein means that compounds of the inventions may exist in one or a mixture of salts and solvate forms. For example a compound of the invention may be substantially pure in one particular salt or solvate form or else may be mixtures of two or more salt or solvate forms.

The present invention provides novel compounds having the general formula I:

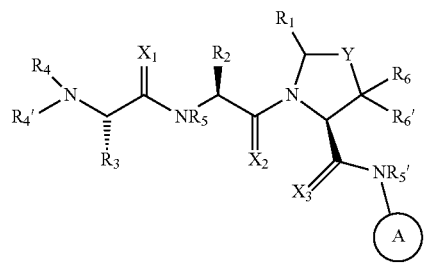

wherein $X_1$, $X_2$, $X_3$, Y, A, $R_1$, $R_2$, $R_3$, $R_4$, $R_4'$, $R_5$, $R_5'$, $R_6$ and $R_6'$ are as described herein.

In a particular embodiment, compounds of the formula I are other than:
L-alanyl-L-valyl-N-phenyl-L-prolinamide;
L-alanyl-L-phenylalanyl-N-(4-nitrophenyl)-L-prolinamide;
L-alanyl-L-alanyl-N-(4-nitrophenyl)-L-prolinamide;
N-acetyl-L-alanyl-L-phenylalanyl-N-(2-chloro-3-pyridinyl)-L-prolinamide;
L-alanyl-L-alanyl-N-(4-nitrophenyl)-L-prolinamide;
N-(4-methoxy-1,4-dioxobutyl)-L-alanyl-L-alanyl-N-[2-[[(phenylamino)carbonyl]-oxy]phenyl]-L-prolinamide;
N-(4-methoxy-1,4-dioxobutyl)-L-alanyl-L-alanyl-N-[4-[[[(1-methylethyl)amino]-carbonyl]oxy]phenyl]-L-prolinamide;
N-(4-methoxy-1,4-dioxobutyl)-L-alanyl-L-alanyl-N-[4-[[(dimethylamino)carbonyl]oxy]-phenyl]-L-prolinamide;
N-(4-methoxy-1,4-dioxobutyl)-L-alanyl-L-alanyl-N-[4-[[(phenylamino)carbonyl]-oxy]phenyl]-L-prolinamide;
N-(3-carboxy-1-oxopropyl)-L-alanyl-L-alanyl-N-(4-nitrophenyl)-L-prolinamide; and
N-[(phenylmethoxy)carbonyl]-L-alanyl-L-alanyl-N-(4-nitrophenyl)-L-prolinamide.

$X_1$ and $X_2$ are each independently O or S. In a preferred embodiment, $X_1$ and $X_2$ are both O. In another preferred embodiment $X_1$ and $X_2$ are both S. In another preferred embodiment, $X_1$ is S while $X_2$ is O. In another preferred embodiment, $X_1$ is O while $X_2$ is S.

Y is $(CHR_7)_n$, O or S; wherein n is 1 or 2 and $R_7$ is H, halogen, alkyl, aryl, aralkyl, amino, arylamino, alkylamino, aralkylamino, alkoxy, aryloxy or aralkyloxy. In a particular embodiment, Y is $CH_2$. In a particular embodiment n is 1. In a particular embodiment n is 1 and Y is $CHR_7$ wherein $R_7$ is aralkyloxy, for example benzyloxy. In a particular embodiment n is 1 and Y is $CHR_7$ wherein $R_7$ is F. In a particular embodiment n is 1 and Y is $CHR_7$ wherein $R_7$ is aralkylamino, for example benzylamino. In another particular embodiment Y is O. In another particular embodiment Y is S.

Ring 'A' is a 6-member aromatic ring or a heteroaromatic ring comprising 1 to 4 nitrogen heteroatoms optionally substituted with amino, hydroxyl, mercapto, halogen, carboxyl, amidino, guanidino, alkyl, alkoxy, aryl, aryloxy, acyl, acyloxy, acylamino, alkoxycarbonylamino, cycloalkyl, alkylthio, alkylsulfinyl, alkylsulfonyl, aminosulfonyl, alkylaminosulfonyl, alkylsulfonylamino or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, alkoxy, haloalkyl, amino, nitro, cyano, cycloalkyl, aryl or a heterocycle. In an embodiment, ring A is optionally substituted with amino, hydroxyl, mercapto, halogen, carboxyl, amidino, guanidino, alkyl, alkoxy, aryl, aryloxy, acyl, acyloxy, acylamino, cycloalkyl or a heterocycle; wherein each alkyl, alkoxy, aryl, aryloxy, acyl, acyloxy, acylamino, cycloalkyl and heterocycle substitution is optionally substituted with hydroxyl, alkoxy, halogen, mercapto, carboxyl, alkyl, haloalkyl, amino, nitro, cycloalkyl, aryl or a heterocycle. In a particular embodiment, ring A is a 6-member aromatic ring optionally substituted as described above. In a particular embodiment, ring A is a 6-member heteroaromatic ring having 1 nitrogen heteroatom and optionally substituted as described above. In a particular embodiment, ring A is a 6-member heteroaromatic ring having 2 nitrogen heteroatoms and optionally substituted as described above. In a particular embodiment ring A has the formula II:

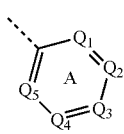

II wherein $Q_1$, $Q_2$, $Q_3$, $Q_4$ and $Q_5$ are independently $CR_9$ or N; wherein $R_9$ is H, amino, hydroxyl, mercapto, halogen, carboxyl, amidino, guanidino, alkyl, alkoxy, aryl, aryloxy, acyl, acyloxy, acylamino, cycloalkyl or a heterocycle; wherein each alkyl, alkoxy, aryl, aryloxy, acyl, acyloxy, acylamino, cycloalkyl and heterocycle substitution is optionally substituted with hydroxyl, halogen, mercapto, carboxyl, alkyl, haloalkyl, amino, nitro, cycloalkyl, aryl or a heterocycle. In a particular embodiment ring A is a group of formula II wherein $Q_4$ is $CR_9$ wherein $R_9$ is aryl or heteroaryl optionally substituted as described above. In a particular embodiment ring A is a group of formula II wherein each of $Q_1$, $Q_2$, $Q_3$, $Q_4$ and $Q_5$ are $CR_9$ wherein each $R_9$ is independent and is defined above. In a particular embodiment, ring A is a group of formula II wherein $Q_1$ is N and $Q_2$, $Q_3$, $Q_4$ and $Q_5$ are each independently $CR_9$. In another embodiment, ring A is a group of formula II wherein $Q_2$ is N and $Q_1$, $Q_3$, $Q_4$ and $Q_5$ are each independently $CR_9$. In another embodiment, ring A is a group of formula II wherein $Q_3$ is N and $Q_1$, $Q_2$, $Q_4$ and $Q_5$ are each independently $CR_9$. In another embodiment, ring A is a group of formula II wherein $Q_1$ and $Q_3$ are both N and $Q_2$, $Q_4$ and $Q_5$ are each independently $CR_9$. In another embodiment, ring A is a group of formula II wherein $Q_1$ and $Q_4$ are both N and $Q_2$, $Q_3$ and $Q_5$ are each independently $CR_9$. In another embodiment, ring A is a group of formula II wherein $Q_1$ and $Q_5$ are both N and $Q_2$, $Q_3$ and $Q_4$ are each independently $CR_9$. In another embodiment, ring A is a group of formula II wherein $Q_2$ and $Q_4$ are both N and $Q_1$, $Q_3$ and $Q_5$ are each independently $CR_9$. In another embodiment, ring A is a group of formula II wherein $Q_1$, $Q_3$ and $Q_5$ are each N and $Q_2$ and $Q_4$ are both independently $CR_9$.

In another embodiment, ring A is phenyl optionally substituted with halogen or hydroxyl, alkyl, alkoxy, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is phenyl substituted with an aryl or heteroaryl group in which said aryl and heteroaryl groups are optionally substituted with hydroxyl, halogen, alkyl and alkoxy. In a particular embodiment, ring A is the group of formula IIa

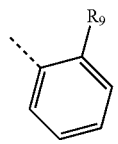

IIa wherein $R_9$ is as defined above. In a particular embodiment, $R_9$ is H, halogen or hydroxyl, alkyl, alkoxy, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In another particular embodiment, $R_9$ is H, halogen or hydroxyl, alkoxy, aryl or heteroaryl wherein said aryl and heteroaryl are optionally substituted with halogen, hydroxyl and alkoxy. In another particular embodiment, $R_9$ is H, fluoro, chloro, methoxy, imidazolyl (e.g. imidazol-2-yl), phenyl, o-chlorophenyl, m-chlorophenyl or pyrimidinyl (e.g. pyrimidin-2-yl or pyrimidin-5-yl).

In another embodiment ring A is pyridinyl group optionally substituted with hydroxyl, alkyl, alkoxy, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is the group of formula IIb-IIIe:

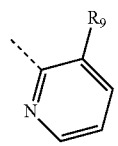

IIb

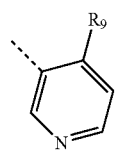

IIc

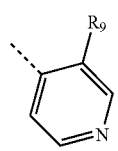

IId

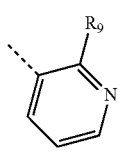

IIe wherein $R_9$ is as defined above. In a particular embodiment, $R_9$ is H, halogen or hydroxyl, alkyl, alkoxy, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In another particular embodiment, $R_9$ is H, halogen or hydroxyl, alkoxy, aryl or heteroaryl wherein said aryl and heteroaryl are optionally substituted with halogen, hydroxyl and alkoxy. In another particular embodiment, $R_9$ is H, fluoro, chloro, methoxy, imidazolyl (e.g. imidazol-2-yl), phenyl, o-chlorophenyl, m-chlorophenyl or pyrimidinyl (e.g. pyrimidin-2-yl or pyrimidin-5-yl). In a particular embodiment, $R_9$ is H, hydroxyl or phenyl.

In another embodiment ring A is pyrimidynyl group optionally substituted with hydroxyl, alkyl, alkoxy, aryl, aralkyl, cycloalkyl, cycloalkylalkyl, a heterocycle or a heterocycle-alkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is the group of formula IIf or IIg:

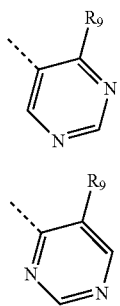

IIf

IIg wherein $R_9$ is as defined above. In a particular embodiment, $R_9$ is H, halogen or hydroxyl, alkyl, alkoxy, aryl, aralkyl, cycloalkyl, cycloalkylalkyl, a heterocycle or a heterocyclealkyl optionally substituted with halogen hydroxyl, mercapto, carboxyl, alkyl, haloalkyl, amino, nitro, aryl or heteroaryl. In another particular embodiment, $R_9$ is H, halogen or hydroxyl, alkoxy, aryl or heteroaryl wherein said aryl and heteroaryl are optionally substituted with halogen, hydroxyl and alkoxy. In another particular embodiment, $R_9$ is H, fluoro, chloro, methoxy, imidazolyl (e.g. imidazol-2-yl), phenyl, o-chlorophenyl, m-chlorophenyl or pyrimidinyl (e.g. pyrimidin-2-yl or pyrimidin-5-yl). In a particular embodiment, $R_9$ is H, hydroxyl or phenyl.

In another embodiment ring A is pyrazinyl group optionally substituted with hydroxyl, alkyl, alkoxy, aryl, aralkyl, cycloalkyl, cycloalkylalkyl, a heterocycle or a heterocyclealkyl optionally substituted with halogen hydroxyl, mercapto, carboxyl, alkyl, haloalkyl, amino, nitro, aryl or heteroaryl. In an embodiment ring A is substituted with an aryl or heteroaryl group. In a particular embodiment, ring A is the group of formula IIh:

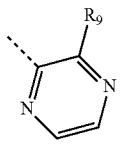

IIh wherein $R_9$ is as defined above. In a particular embodiment, $R_9$ is H, halogen or hydroxyl, alkyl, alkoxy, aryl, aralkyl, cycloalkyl, cycloalkylalkyl, a heterocycle or a heterocyclealkyl optionally substituted with halogen hydroxyl, mercapto, carboxyl, alkyl, haloalkyl, amino, nitro, aryl or heteroaryl. In another particular embodiment, $R_9$ is H, halogen or hydroxyl, alkoxy, aryl or heteroaryl wherein said aryl and heteroaryl are optionally substituted with halogen, hydroxyl and alkoxy. In another particular embodiment, $R_9$ is H, fluoro, chloro, methoxy, imidazolyl (e.g. imidazol-2-yl), phenyl, o-chlorophenyl, m-chlorophenyl or pyrimidinyl (e.g. pyrimidin-2-yl or pyrimidin-5-yl). In a particular embodiment, $R_9$ is H, hydroxyl or phenyl.

$R_1$ is H or $R_1$ and $R_2$ together form a 5-8 member ring. In a particular embodiment, $R_1$ is H. In a particular embodiment, $R_1$ and $R_2$ together form a 6-member ring. In a particular embodiment, $R_1$ and $R_2$ together form a 7-member ring. In another particular embodiment, $R_1$ and $R_2$ together form an 8-member ring. In another particular embodiment, $R_1$ and $R_2$ together form a 7-member ring while Y is S. In another particular embodiment, $R_1$ is H, while Y is $CH_2$. In another particular embodiment, $R_1$ is H, while Y is S. In another particular embodiment, $R_1$ is H, while Y is O.

$R_2$ is alkyl, cycloalkyl, cycloalkylalkyl, aryl, aralkyl, a heterocycle or heterocyclylalkyl. In a preferred embodiment $R_2$ is alkyl or cycloalkyl. In an embodiment, each $R_2$ group is each optionally substituted with hydroxyl, mercapto, halogen, amino, carboxyl, alkyl, haloalkyl, alkoxy or alkylthio; In an embodiment of the invention $R_2$ is t-butyl, isopropyl, cyclohexyl, cyclopentyl or phenyl. In a particular embodiment, $R_2$ is cyclohexyl. In another embodiment $R_2$ is tetrahydropyran-4-yl. In another particular embodiment, $R_2$ is isopropyl (i.e. the valine amino acid side chain). In another particular embodiment, $R_2$ is t-butyl. In a particular embodiment $R_2$ is oriented such that the amino acid, or amino acid analogue, which it comprises is in the L-configuration.

$R_3$ is H or alkyl. In a preferred embodiment $R_3$ is H or methyl, ethyl, propyl or isopropyl. In a particularly preferred embodiment $R_3$ is H or methyl. In a most preferred embodiment $R_3$ is methyl. In another particular embodiment, $R_3$ is t-butyl. In a preferred embodiment $R_3$ is oriented such that the amino acid, or amino acid analogue, which it comprises is in the L-configuration.

$R_4$ and $R_4'$ are independently H, hydroxyl, amino, alkyl, aryl, aralkyl, cycloalkyl, cycloalkylalkyl, heteroaryl, or heteroarylalkyl wherein each alkyl, aryl, aralkyl, cycloalkyl, cycloalkylalkyl, heteroaryl and heteroarylalkyl is optionally substituted with halogen, hydroxyl, mercapto, carboxyl, alkyl, alkoxy, amino and nitro. In a particular embodiment $R_4$ and $R_4'$ are both H. In another particular embodiment $R_4$ is methyl and $R_4'$ is H. In a particular embodiment one of $R_4$ and $R_4'$ is hydroxyl (OH) while the other is H. In another embodiment, one of $R_4$ and $R_4'$ is amino, such as $NH_2$, NHMe and NHEt, while the other is H. In a particular embodiment, $R_4'$ is H and $R_4$ is H, alkyl, aryl, aralkyl, cycloalkyl, cycloalkylalkyl, heteroaryl or heteroarylalkyl. In a particular embodiment $R_4$ is a group selected from the group consisting of:

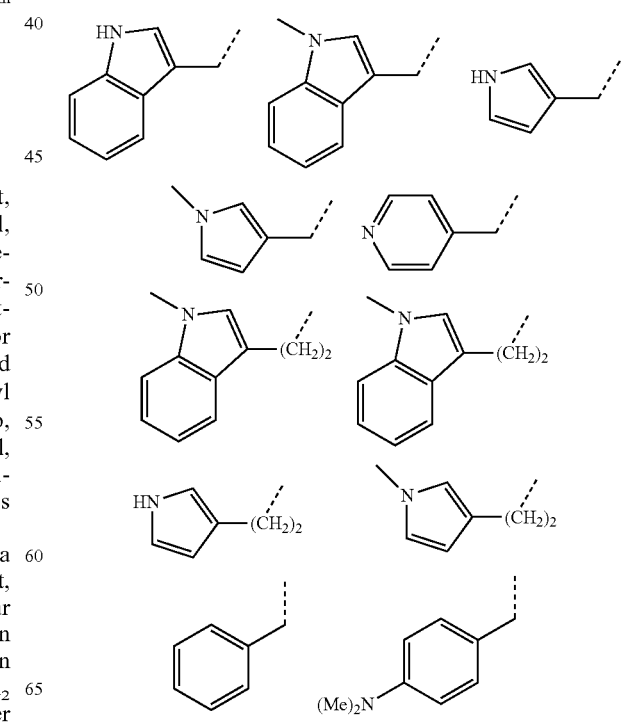

-continued

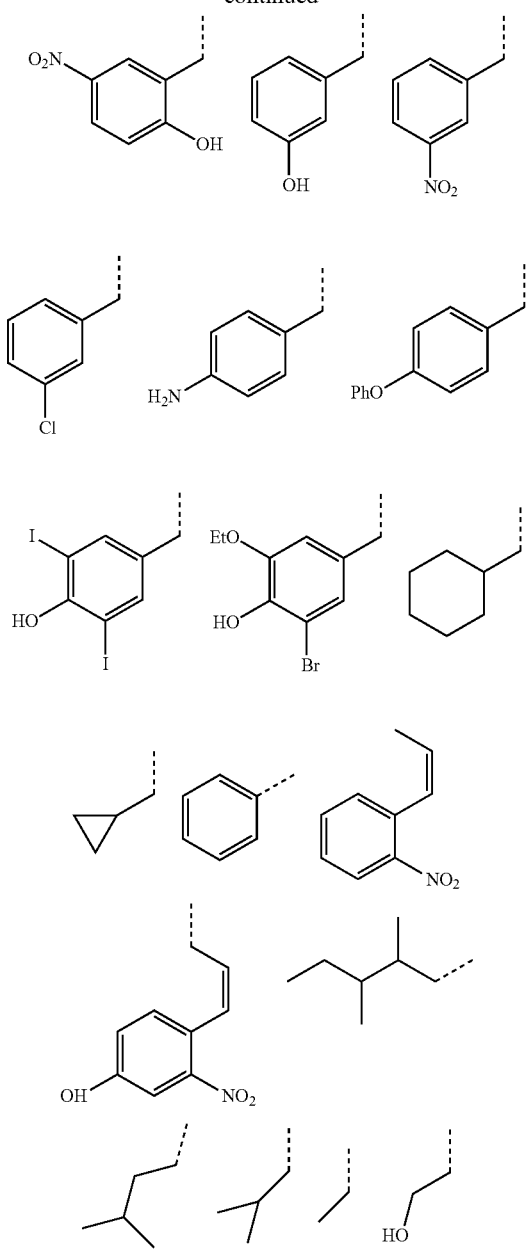

$R_5$ and $R_5'$ are each independently H or alkyl. In a preferred embodiment, $R_5$ and $R_5'$ are H or methyl. In a particular embodiment, $R_5$ is H and $R_5'$ is methyl. In another particular embodiment, $R_5$ is methyl and $R_5'$ is H. In another particular embodiment $R_5$ and $R_5'$ are both methyl. In another particular embodiment, $R_5$ and $R_5'$ are both H.

$R_6$, and $R_6'$ are each independently H, alkyl, aryl or aralkyl. In a particular embodiment, $R_6$ is alkyl, for example methyl. In another particular embodiment $R_6$ is aryl, for example phenyl. In another particular embodiment $R_6$ is aralkyl, for example benzyl. In a particular embodiment $R_6$ and $R_6'$ are the same, for example both alkyl, e.g. both methyl. In another particular embodiment $R_6$ is methyl and $R_6'$ is H. In another particular embodiment $R_6$ and $R_6'$ are both H.

In another aspect of the invention there is provided a dimer compound of the general formula IIIa:

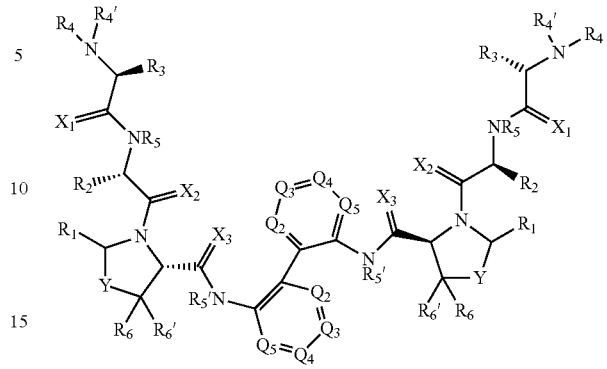

wherein $X_1$, $X_2$, $X_3$, Y, A, $R_1$, $R_2$, $R_3$, $R_4$, $R_4'$, $R_5$, $R_5'$, $R_6$, $R_6'$, $Q_2$, $Q_3$, $Q_4$ and $Q_5$ are in each instance independently as described herein.

In another aspect of the invention there is provided a dimer compound of the general formula IIIb:

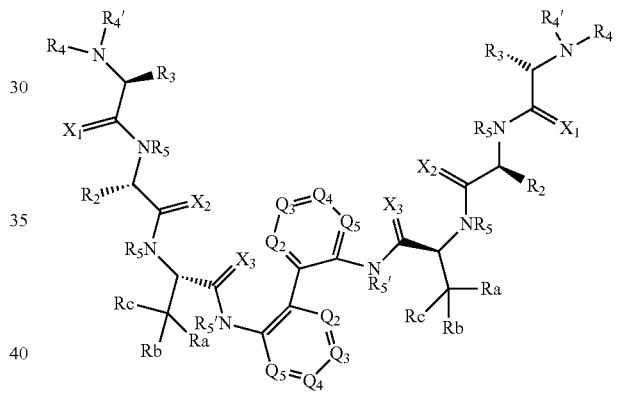

wherein $X_1$, $X_2$, $X_3$, $R_2$, $R_3$, $R_4$, $R_4'$, $R_5$, $R_5'$, $R_6$, $R_6'$, $Q_2$, $Q_3$, $Q_4$ and $Q_5$ are in each instance independently as described herein, and $R_a$, $R_b$ and $R_c$ are each independently hydroxyl, halogen, alkyl, alkoxy, alkylthio or sulfonyl; wherein said alkyl, alkoxy, alkylthio and sulfonyl groups are optionally substituted with amido, carbamoyl and aryl which are optionally substituted with hydroxyl halogen and alkoxy; or two of $R_a$, $R_b$ and $R_c$ together form a carbocycle or heterocycle and the other of $R_a$, $R_b$ and $R_c$ is H, hydroxyl, halogen, alkyl, alkoxy, alkylthio or sulfonyl. Alternatively, $R_a$ is H while $R_b$ and $R_c$ are each independently hydroxyl, halogen, alkyl, alkoxy, alkylthio or sulfonyl; wherein said alkyl, alkoxy, alkylthio and sulfonyl groups are optionally substituted with amido, carbamoyl and aryl which are optionally substituted with hydroxyl halogen and alkoxy; or two of $R_a$, $R_b$ and $R_c$ together form a carbocycle or heterocycle and the other of R., $R_b$ and $R_c$ is H, hydroxyl, halogen, alkyl, alkoxy, alkylthio or sulfonyl. In a particular embodiment $R_a$, $R_b$ and $R_c$ are each methyl, halogen, methoxy, hydroxy, methylthio, methylsulfonyl. In a particular embodiment $R_a$, $R_b$ and $R_c$ are each methyl. In a particular embodiment $R_a$, $R_b$ and $R_c$ are each F. In a particular embodiment two of $R_a$, $R_b$ and $R_c$ are methyl and the other is F. In a particular embodiment two of $R_a$, $R_b$ and $R_c$ are methyl and the other is hydroxyl. In a particular embodiment two of $R_a$, $R_b$ and $R_c$ are methyl and the other is methoxy. In a particular embodiment two of $R_a$, $R_b$ and $R_c$ are methyl and the other is methyl sulfonyl. In a particular embodiment two of $R_a$, $R_b$ and $R_c$ are methyl and the other is methylthio. In a particular embodiment two of $R_a$, $R_b$ and $R_c$ are methyl and the other is 4-methoxybenzylthio. In a particular embodiment two of $R_a$, $R_b$ and $R_c$ are methyl and the other is acetamidomethylthio. In a particular embodiment two of $R_a$, $R_b$ and $R_c$ together form a carbocycle or heterocycle while the other of $R_a$, $R_b$ and $R_c$ is H, hydroxyl, halogen, alkyl, alkoxy, alkylthio or sulfonyl. In a particular embodiment two of $R_a$, $R_b$ and $R_c$ form a heterocycle. In a particular embodiment two of $R_a$, $R_b$ and $R_c$ form a pyran. In a particular embodiment two of $R_a$, $R_b$ and $R_c$ form a pyran while the other is H. In a particular embodiment two of $R_a$, $R_b$ and $R_c$ form a pyran while the other is methyl.

Alternatively, $R_a$ is H while $R_b$ and $R_c$ are each independently hydroxyl, halogen, alkyl, alkoxy, alkylthio or sulfonyl; wherein said alkyl, alkoxy, alkylthio and sulfonyl groups are optionally substituted with amido, carbamoyl and aryl which are optionally substituted with hydroxyl halogen and alkoxy; or two of $R_a$, $R_b$ and $R_c$ together form a carbocycle or heterocycle and the other of $R_a$, $R_b$ and $R_c$ is H, hydroxyl, halogen, alkyl, alkoxy, alkylthio or sulfonyl; provided that the compound of the invention is other than 2-acetamido-N-(1-(1-(furan-2-yl)-2-methylpropyl-amino)-1-oxopropan-2-yl)propanamide. When $R_a$ is H, $R_b$ and $R_c$ may be each of the particular embodiments described previously while Ra is H provided that the compound of the invention is other than 2-acetamido —N-(1-(1-(furan-2-yl)-2-methylpropyl-amino)-1-oxopropan-2-yl)propan-amide. In a particular embodiment $R_a$ is H and $R_b$ and $R_c$ are each methyl provided that the compound of the invention is other than 2-acetamido-N-(1-(1-(furan-2-yl)-2-methylpropyl-amino)-1-oxopropan-2-yl)propanamide.

Compounds of the invention contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

The invention also encompasses prodrugs of the compounds described above. Suitable prodrugs where applicable include known amino-protecting and carboxy-protecting groups which are released, for example hydrolyzed, to yield the parent compound under physiologic conditions. A particular class of prodrugs are compounds in which a nitrogen atom in an amino, amidino, aminoalkyleneamino, iminoalkyleneamino or guanidino group is substituted with a hydroxy (OH) group, an alkylcarbonyl (—CO—R) group, an alkoxycarbonyl (—CO—OR), an acyloxyalkyl-alkoxycarbonyl (—CO—O—R—O—CO—R) group where R is a monovalent or divalent group and as defined above or a group having the formula —C(O)—O—CP1P2-haloalkyl, where P1 and P2 are the same or different and are H, lower alkyl, lower alkoxy, cyano, halo lower alkyl or aryl. In a particular embodiment, the nitrogen atom is one of the nitrogen atoms of the amidino group of the compounds of the invention. These prodrug compounds are prepared reacting the compounds of the invention described above with an activated acyl compound to bond a nitrogen atom in the compound of the invention to the carbonyl of the activated acyl compound. Suitable activated carbonyl compounds contain a good leaving group bonded to the carbonyl carbon and include acyl halides, acyl amines, acyl pyridinium salts, acyl alkoxides, in particular acyl phenoxides such as p-nitrophenoxy acyl, dinitrophenoxy acyl, fluorophenoxy acyl, and difluorophenoxy acyl. The reactions are generally exothermic and are carried out in inert solvents at reduced temperatures such as −78 to about 50 C. The reactions are usually also carried out in the presence of an inorganic base such as potassium carbonate or sodium bicarbonate, or an organic base such as an amine, including pyridine, triethylamine, etc. One manner of preparing prodrugs is described in U.S. Ser. No. 08/843,369 filed Apr. 15, 1997 (corresponding to PCT publication WO9846576) the contents of which are incorporated herein by reference in their entirety.

Particular compounds of formula I include the following:

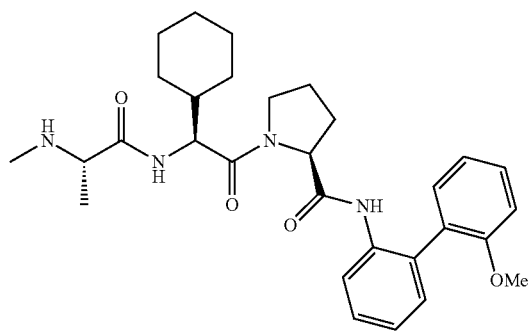

1

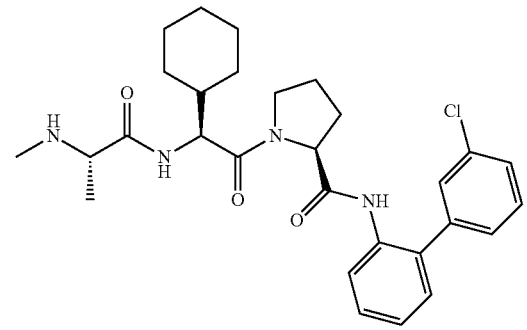

2

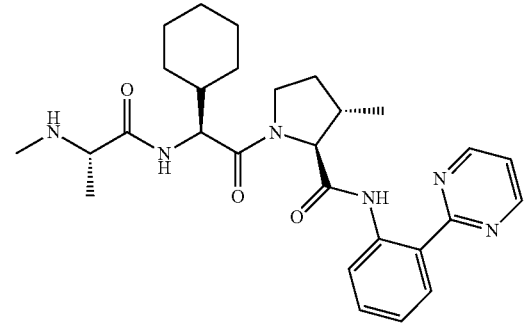

3

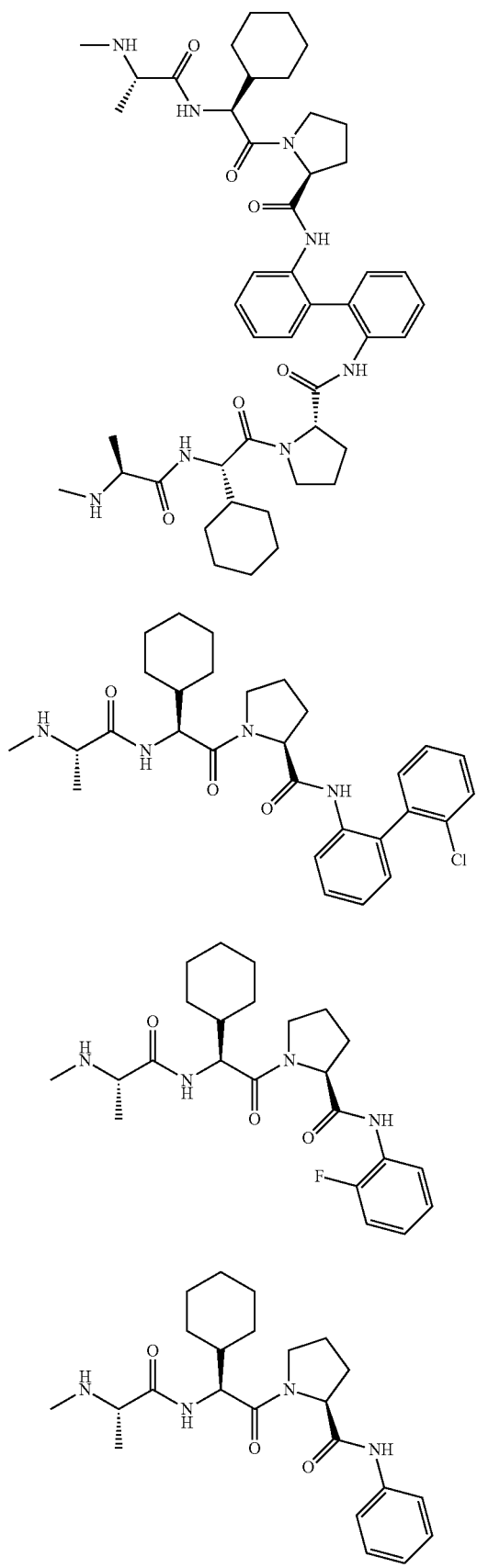
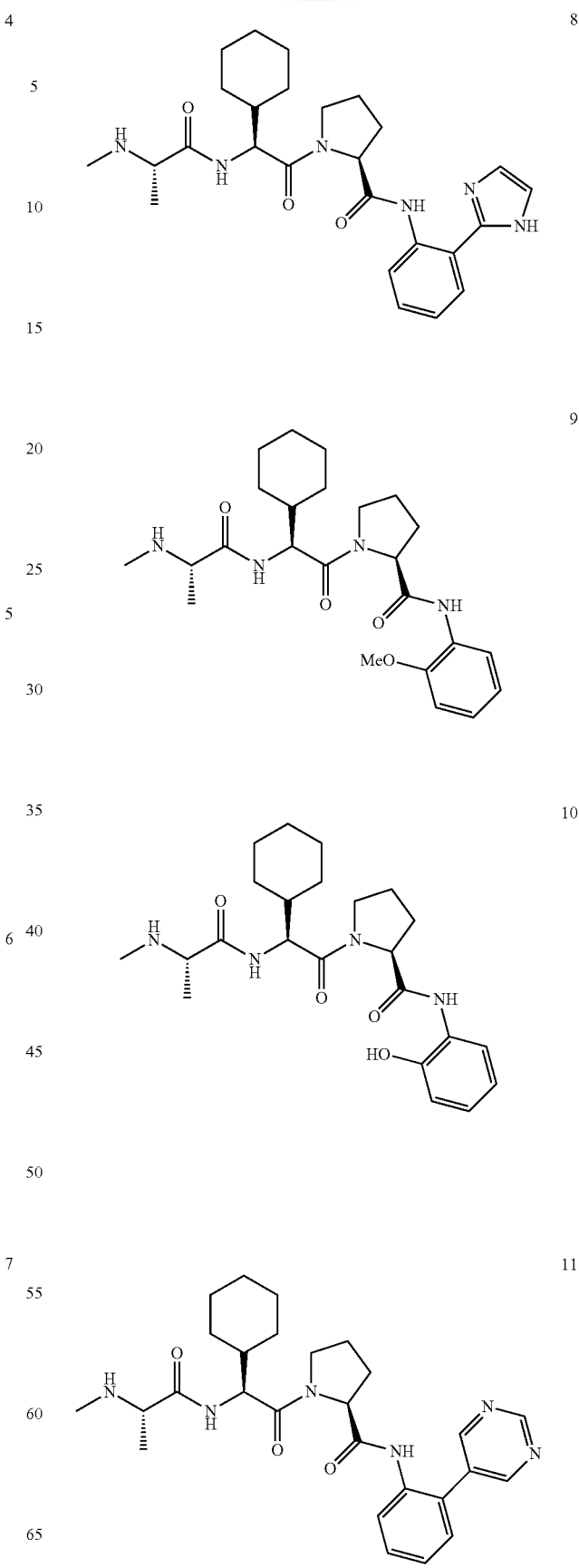

12
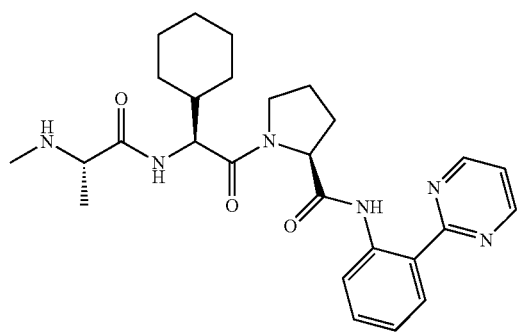
13
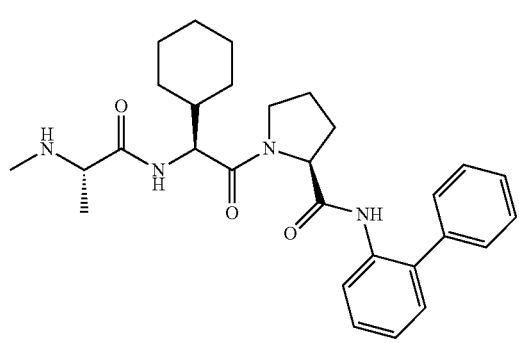
14
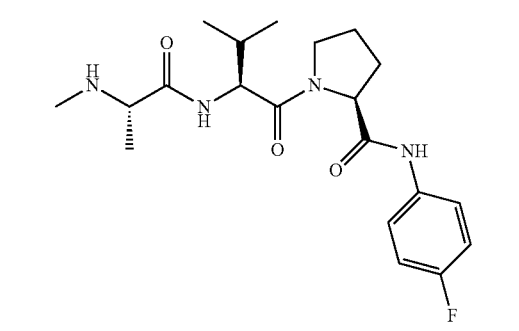
15
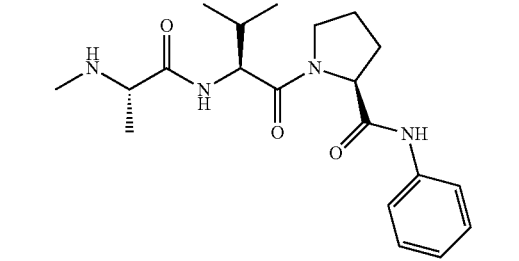
16
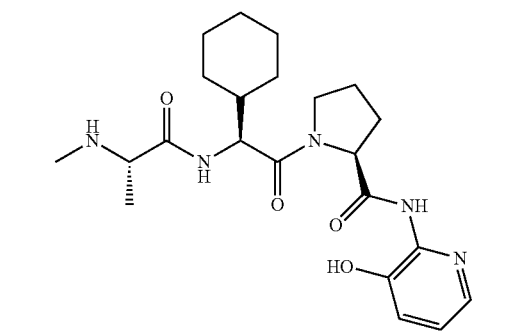
17
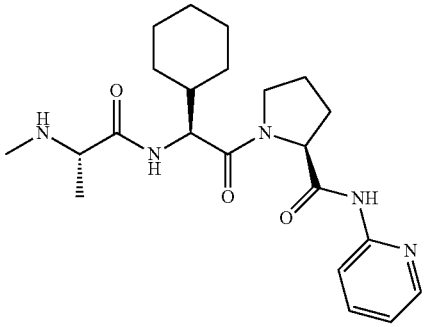
18
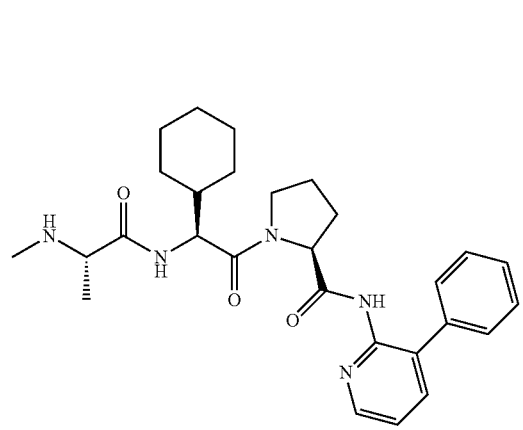
19
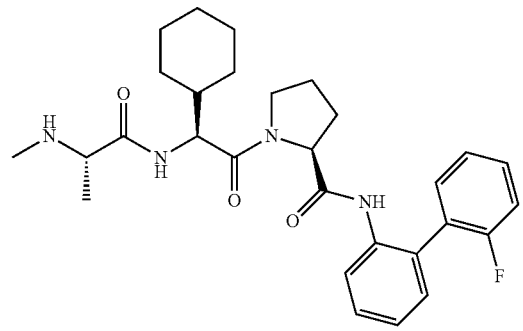
20
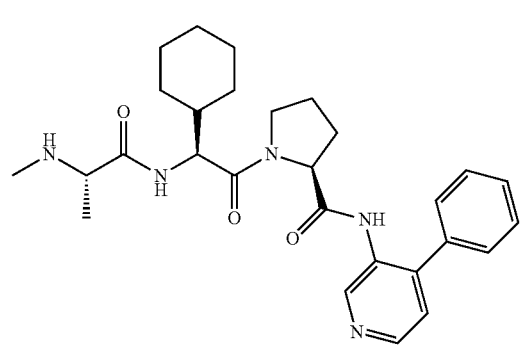

-continued

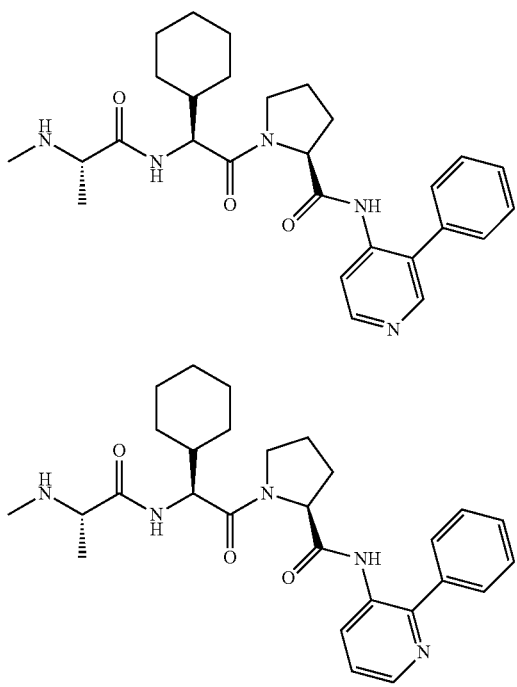

Synthesis

Compounds of the invention are prepared using standard organic synthetic techniques from commercially available starting materials and reagents. It will be appreciated that synthetic procedures employed in the preparation of compounds of the invention will depend on the particular substituents present in a compound and that various protection and deprotection may be required as is standard in organic synthesis. In a general synthetic scheme compounds of the invention may be prepared using typical peptide chemistry techniques by coupling the amino acid residue analogues with typical amide coupling procedures. In scheme 1, amine-protected amino acid residue analogues are coupled and deprotected sequentially to give the final compounds.

Scheme 1

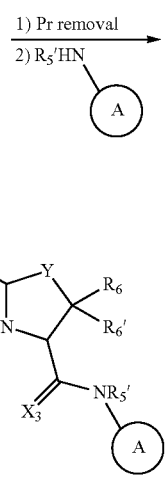

It will be appreciated that the amino acid analogs may be coupled any order and may be prepared using solid phase support which is routine in the art.

Compounds of the invention in which $R_4$ or $R_4'$ are other than H may be prepared according to standard organic chemistry techniques, for example by reductive amination in which a starting amino acid residue analog e.g. $NH_2$—$CH(R_3)$—$C(O)$—$OH$ is reacted with a suitable aldehyde or ketone to give the desired $R_4$ and $R_4'$ substituents. See scheme 14. The resulting $R_4/R_4'$ substituted amino acid intermediate can then be conjugated to the next amino acid intermediate or the remainder of the compound using standard peptide coupling procedures.

Scheme 2

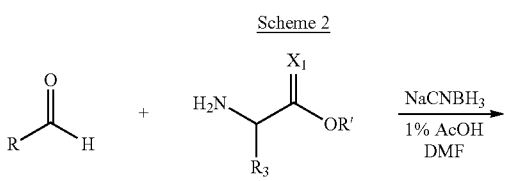

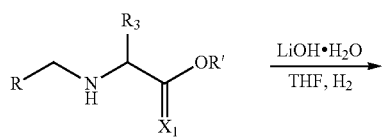

In a particular embodiment, alanine is reacted with 1-methylindole-2-carboxaldehyde and reduced with sodium cyanoborohydride dissolved in 1% HOAc/DMF to give the N-substituted alanine residue which may be used in preparing compounds of the invention. See scheme 15.

Scheme 3

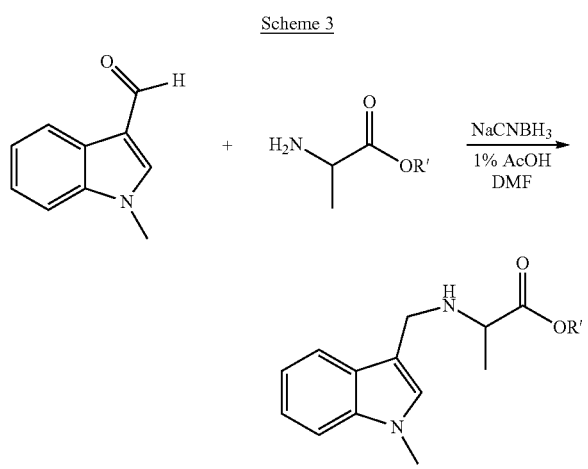

Alternatively, the reductive amination procedure to introduce $R_4/R_4'$ substituents is the final step in the preparation of the compound.

When compounds of the invention incorporate $R_4$ or $R_4'$ substituents other than H, they may also be prepared by substitution of a suitable acid intermediate which incorporates a leaving group with a desired amine For example Br—CH($R_3$)—C(O)—OH is substituted with an amine $R_4$—$NH_2$ or $R_4$—NH—$R_4'$ according to scheme 16.

Scheme 4

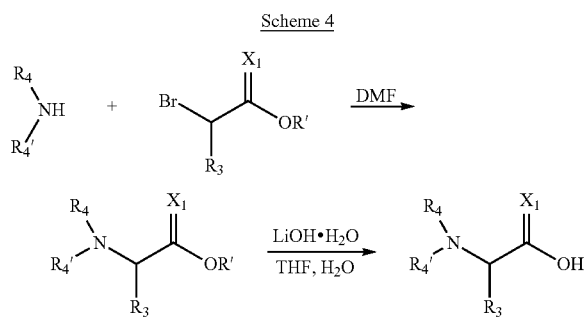

Alternatively, the substitution reaction introducing $R_4$ or $R_4'$ substituents may be performed as a final step in the preparation of the compound as illustrated in scheme 17.

Scheme 5

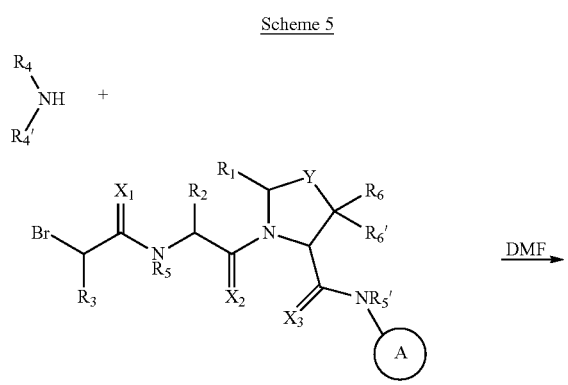

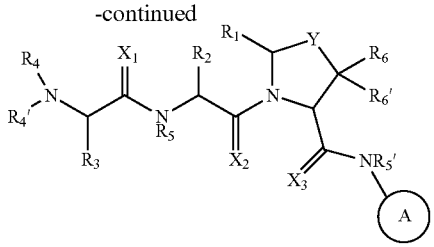

In a particular embodiment, 2-bromopropionic acid is reacted with the following amines dissolved in DMF and bubbled for until substitution is complete to form N-substituted alanine residues:

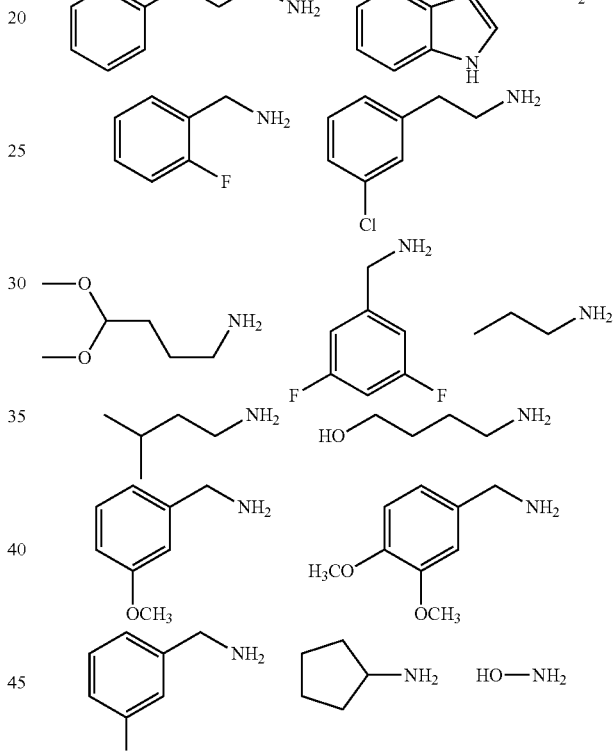

Compounds of the invention in which any one or more of $X_1$, $X_2$ and $X_3$ are sulfur, i.e. the compound incorporates a thioamide, may be prepared according to established organic chemistry techniques. For example, compounds in which $X_2$ is sulfur can be prepared according to scheme 18 starting from an Fmoc protected amino acid residue analog $NH_2$—CH($R_2$)—COOH which is dissolved in THF and cooled to −25° C., with addition of DIPEA followed by addition of isobutylchloroformate. After 10 minutes, the diamine, 4-nitrobenzene-1,2-diamine, is added and the reaction mixture is continuously stirred at −25° C. for 2 hours, then at room temperature overnight. THF is vacuumed off and the mixture is then subjected to flash chromatography using 50% EtOAc/Hexane to yield the product. The Fmoc-alanine derivative, phosphorus pentasulfide and sodium carbonate are mixed in THF and stirred overnight. The solution is concentrated and direct chromatography using 80% EtOAc/Hexane yields the activated thioalanine. The activated thioalanine and sodium nitrite are then mixed in acetic acid and diluted with H₂O. The resulting precipitant is filtered and dried to yield the product. The thioalanine is coupled to an OH-protected proline amino acid residue analog by dissolving both in DMF. The thioamide product may then be deprotected with 20% PIP/DMA for 15 minutes and used to conjugate to the $R_4/R_4'$—N—CH($R_3$)—COOH amino acid residue analog followed by OH-deprotection and coupling to an amino-substituted A ring intermediate. Alternatively the Fmoc-protected thioamide is first coupled to an amino substituted A ring intermediate followed by Fmoc deprotection and subsequent coupling to the $R_4/R_4'$—N—CH($R_3$)—COOH amino acid residue analog.

coupling techniques. For example, particular compounds of the invention in which $R_9$ is aryl or heteroaryl may be prepared according to scheme 7.

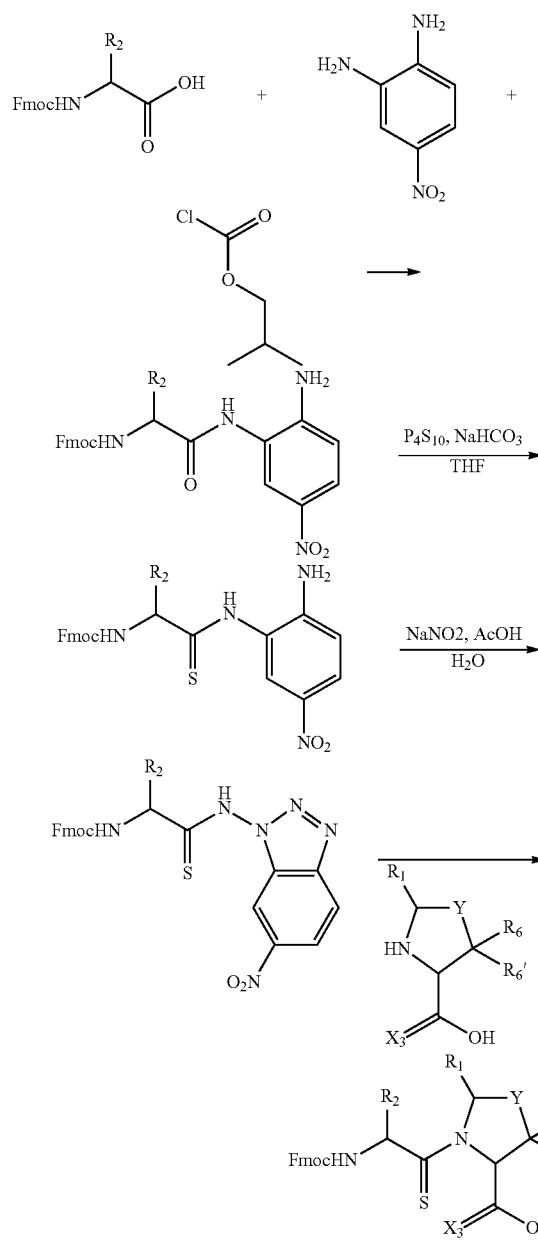

Scheme 6

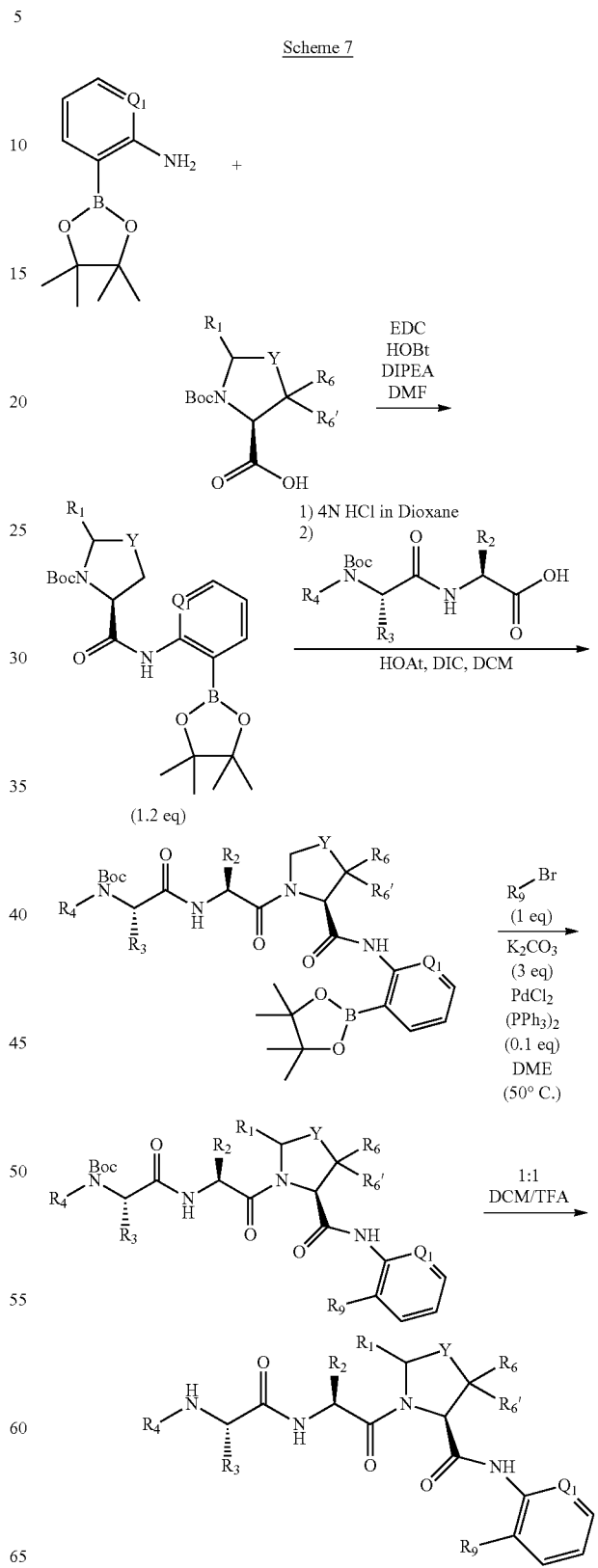

Scheme 7

In a particular embodiment when $R_9$ is aryl or heteroaryl, compounds of the invention may be prepared using Suzuki Indications The compounds of the invention inhibit the binding of IAP proteins to caspases, in particular X-IAP binding interaction with caspases 3 and 7. The compounds also inhibit the binding of ML-IAP to Smac protein. Accordingly, the compounds of the invention are useful for inducing apoptosis in cells or sensitizing cells to apoptotic signals, in particular cancer cells. Compounds of the invention are useful for inducing apoptosis in cells that overexpress IAP proteins. Alternatively, compounds of the invention are useful for inducing apoptosis in cells in which the mitochondrial apoptotic pathway is disrupted such that release of Smac from ML-IAP proteins is inhibited, for example by up regulation of Bcl-2 or down regulation of Bax/Bak. More broadly, the compounds can be used for the treatment of all cancer types which fail to undergo apoptosis. Examples of such cancer types include neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

In an embodiment, compounds of the invention selectively bind cIAP1 relative to XIAP as measured in a binding assay such as a Time-Resolved Fluorescence Resonance Energy Transfer (TR-FRET assay or a Fluorescence Polarization assay as described herein. In a particular embodiment, compounds of the invention have >10-fold selective binding to cIAP1 relative to XIAP. In another particular embodiment, compounds of the invention have >100-fold selective binding to cIAP1. In a particular embodiment, compounds of the invention have >1000-fold selective binding to cIAP1.

Compounds of the invention are useful for sensitizing cells to apoptotic signals. Accordingly, the compounds may be administered prior to, concomitantly with, or following administration of radiation therapy or cytostatic or antineoplastic chemotherapy. Suitable cytostatic chemotherapy compounds include, but are not limited to (i) antimetabolites, such as cytarabine, fludarabine, 5-fluoro-2'-deoxyuiridine, gemcitabine, hydroxyurea or methotrexate; (ii) DNA-fragmenting agents, such as bleomycin, (iii) DNA-crosslinking agents, such as chlorambucil, cisplatin, cyclophosphamide or nitrogen mustard; (iv) intercalating agents such as adriamycin (doxorubicin) or mitoxantrone; (v) protein synthesis inhibitors, such as L-asparaginase, cycloheximide, puromycin or diphtheria toxin; (Vi) topoisomerase I poisons, such as camptothecin or topotecan; (vii) topoisomerase II poisons, such as etoposide (VP-16) or teniposide; (viii) microtubule-directed agents, such as colcemid, colchicine, paclitaxel, vinblastine or vincristine; (ix) kinase inhibitors such as flavopiridol, staurosporin, STI571 (CPG 57148B) or UCN-01 (7-hydroxystaurosporine); (x) miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; (xi) hormones such as glucocorticoids or fenretinide; (xii) hormone antagonists, such as tamoxifen, finasteride or LHRH antagonists. In a preferred embodiment, compounds of the present invention are coadministered with a cytostatic compound selected from the group consisting of cisplatin, doxorubicin, taxol, taxotere and mitomycin C. Most preferred, the cytostatic compound is doxorubicin.

Another class of active compounds which can be used in the present invention are those which are able to sensitize for or induce apoptosis by binding to death receptors ("death receptor agonists"). Such agonists of death receptors include death receptor ligands such as tumor necrosis factor a (TNF-α), tumor necrosis factor β (TNF-β, lymphotoxin-α), LT-β (lymphotoxin-β), TRAIL (Apo2L, DR4 ligand), CD95 (Fas, APO-1) ligand, TRAMP (DR3, Apo-3) ligand, DR6 ligand as well as fragments and derivatives of any of said ligands. Preferably, the death receptor ligand is TNF-α. More preferably the death receptor ligand is Apo2L/TRAIL. Furthermore, death receptors agonists comprise agonistic antibodies to death receptors such as anti-CD95 antibody, anti-TRAIL-R1 (DR4) antibody, anti-TRAIL-R2 (DR5) antibody, anti-TRAIL-R3 antibody, anti-TRAIL-R4 antibody, anti-DR6 antibody, anti-TNF-R1 antibody and anti-TRAMP (DR3) antibody as well as fragments and derivatives of any of said antibodies.

For the purpose of sensitizing cells for apoptosis, the compounds of the present invention can be also used in combination with radiation therapy. The phrase "radiation therapy" refers to the use of electromagnetic or particulate radiation in the treatment of neoplasia. Radiation therapy is based on the principle that high-dose radiation delivered to a target area will result in the death of reproducing cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. Examples of radiotherapeutic agents are provided in, but not limited to, radiation therapy and is known in the art (Hellman, Principles of Radiation Therapy, Cancer, in Principles I and Practice of Oncology, 24875 (Devita et al., 4th ed., vol 1, 1993). Recent advances in radiation therapy include three-dimensional conformal external beam radiation, intensity modulated radiation therapy (IMRT), stereotactic radiosurgery and brachytherapy (interstitial radiation therapy), the latter placing the source of radiation directly into the tumor as implanted "seeds". These newer treatment modalities deliver greater doses of radiation to the tumor, which accounts for their increased effectiveness when compared to standard external beam radiation therapy.

Ionizing radiation with beta-emitting radionuclides is considered the most useful for radiotherapeutic applications because of the moderate linear energy transfer (LET) of the ionizing particle (electron) and its intermediate range (typically several millimeters in tissue). Gamma rays deliver dosage at lower levels over much greater distances. Alpha particles represent the other extreme, they deliver very high LET dosage, but have an extremely limited range and must, therefore, be in intimate contact with the cells of the tissue to be treated. In addition, alpha emitters are generally heavy metals, which limits the possible chemistry and presents undue hazards from leakage of radionuclide from the area to be treated. Depending on the tumor to be treated all kinds of emitters are conceivable within the scope of the present invention.

Furthermore, the present invention encompasses types of non-ionizing radiation like e.g. ultraviolet (UV) radiation, high energy visible light, microwave radiation (hyperthermia therapy), infrared (IR) radiation and lasers. In a particular embodiment of the present invention UV radiation is applied.

The invention also includes pharmaceutical compositions or medicaments containing the compounds of the invention and a therapeutically inert carrier, diluent or excipient, as well as methods of using the compounds of the invention to prepare such compositions and medicaments. Typically, the compounds of formula I used in the methods of the invention are formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. Formulation in an acetate buffer at pH 5 is a suitable embodiment. The inhibitory compound for use herein is preferably sterile. The compound ordinarily will be stored as a solid composition, although lyophilized formulations or aqueous solutions are acceptable.

The composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit IAP interaction with caspases, induce apoptosis or sensitize a malignant cell to an apoptotic signal. Such amount is preferably below the amount that is toxic to normal cells, or the mammal as a whole.

Generally, the initial pharmaceutically effective amount of the compound of the invention administered parenterally per dose will be in the range of about 0.01-100 mg/kg, preferably about 0.1 to 20 mg/kg of patient body weight per day, with the typical initial range of compound used being 0.3 to 15 mg/kg/day. Oral unit dosage forms, such as tablets and capsules, preferably contain from about 25 to about 1000 mg of the compound of the invention.

The compound of the invention may be administered by any suitable means, including oral, topical, transdermal, parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution is typically filtered, e.g. using a 0.2 micron filter, to remove impurities and contaminants

EXAMPLES

The invention will be more fully understood by reference to the following examples. They should not, however, be construed as limiting the scope of the invention. Abbreviations used herein are as follows:

ACN: acetonitrile;

Chg: cyclohexylglycine;

DCM: dichloromethane;

DIBoc: di-t-butyldicarbonate

DIPEA: diisopropylethylamine;

DMAP: 4-dimethylaminopyridine;

DME: 1,2-dimethoxyethane;

DMF: dimethylformamide;

DMSO: dimethylsulfoxide

EDC: 1-ethyl-3-(3-dimethylaminopropyl)carbodiimide;

EEDQ: 2-ethoxy-1-ethoxycarbonyl-1,2-dihydroquinoline

LCMS: liquid chromatography mass spectrometry;

HATU: O-(7-Azobenzotriazol-1-yl)-1,1,3,3-tetramethyluronium hexafluorophosphate;

HOBt: N-Hydroxybenzotriazole

HBTU: 2-(1H-Benzotriazol-1-yl)-1,1,3,3-Tetramethyl-uronium Hexafluorophosphate

HPLC: high performance liquid chromatography;

NBS: N-bromosuccinamide;

TASF: tris(dimethylamino)sulfonium difluorotrimethylsilicate;

TEA: triethylamine;

TFA: trifluoroacetate;

THF: tetrahydrofuran;

Example 1

6-(1,3-Dioxo-1,3-dihydro-isoindol-2-yl)-5-oxo-octahydro-thiazolo[3,2-a]azepine-3-carboxylic acid ethyl ester

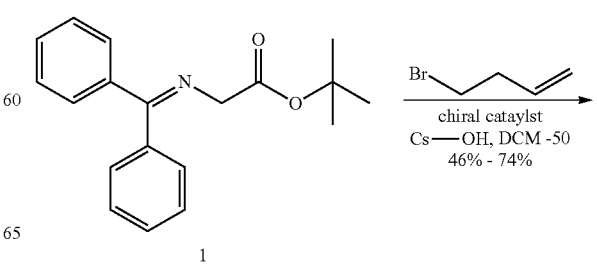

-continued

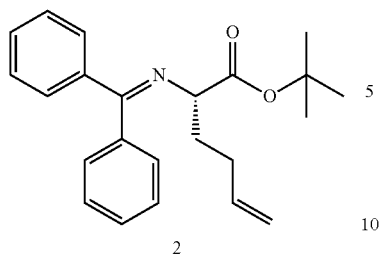

2

To a stirred solution of N-(Diphenylmethylene) glycine t-butyl ester 1 (3.0 g, 10.1 mmol) and chiral catalyst O-Allyl-N-(9-anthracenylmethyl)-cinchonidium bromide (613 mg, 1.0 mmol) in dry DCM (30 mL) was added cesium hydroxide (17 g, 101 mmol). The reaction was cooled to −78° C. in a dry ice acetone bath and 4-bromo-1-butene was added dropwise. After addition the reaction was stirred vigorously under N₂ at −48° C. for 48 hours. Ethyl ether was added followed by H₂O. The organic layer was seperated and washed 2× with H₂O, 1× brine, dried with MgSO₄ and concentrated. The product was purified by SiO₂ chromatography over a gradient of 0-10% EtOAc in Hexanes to give 2 in 65% yield.

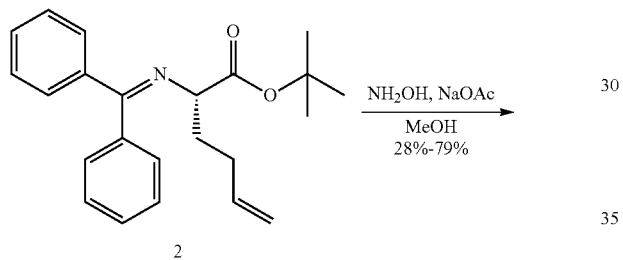

To a stirred solution of 2 (1.52 g, 4.3 mmol) in dry MeOH (50 mL) was added NaOAc (720 mg, 8.6 mmol) and NH₂OH.HCl (540 mg, 7.6 mmol). Stirred under N₂ at room temperature for 2 hours. DCM and 0.1 N NaOH were added. The aqueous layer was separated and extracted 3× with DCM, dried with Na₂SO₄ and the DCM fractions were combined and concentrated. The product was purified by SiO₂chromatography, 0-10% MeOH in DCM with 0.05% TEA to give 3 in 70% yield.

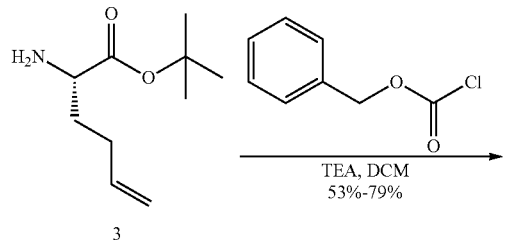

-continued

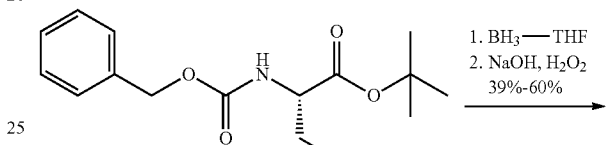

4

To a solution of 3 (610 mg, 3.3 mmol) in dry DCM (20 mL) was added triethylamine (550 μL, 3.9 mmol) and benzyl chloroformate (550 μL, 3.9 mmol). The reaction was stirred at room temperature for 2 hours. The solution was concentrated and purified by SiO₂ chromatography over a gradient of 0-30% EtOAc in Hexanes to give 4 in 66% yield.

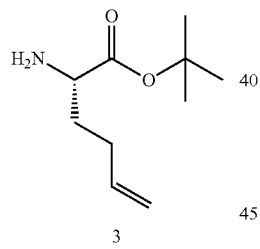

4

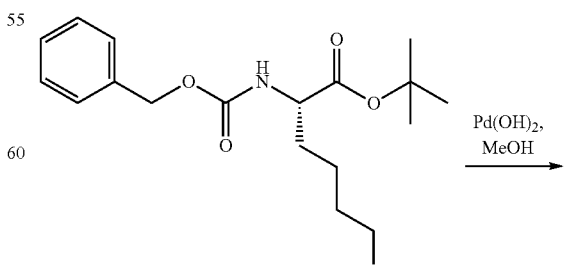

5

To a stirred solution of 4 (577 mg, 1.8 mmol) in THF (20 mL) under N₂ was added BH₃.THF. After 1 hour 3 N NaOH (300 μL, 0.9 mmol) and H₂O₂ (306 μL, 2.7 mmol) was added. The reaction was stirred overnight and subsequently diluted with H₂O, extracted 2× with ethyl ether, dried with MgSO₄ and concentrated. The product was purified by SiO₂ chromatography over a gradient of 10-45% EtOAc in Hexanes to give 5 in 50% yield.

5

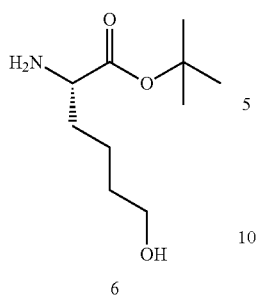

5

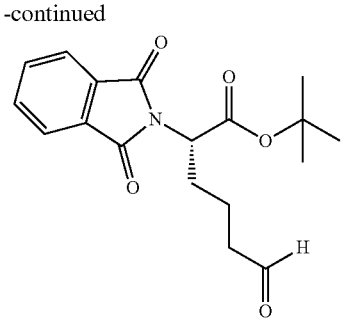

8

To a stirred solution of 5 (71 mg, 0.21 mmol) in MeOH (2 mL) under 1 atm H₂ 10% palladium hydroxide on carbon (30 mg) was added. The reaction was complete after 30 minutes. The reaction was filtered over Celite and concentrated to give 6 in quantitative yield.

Oxalyl chloride (561 µL, 6.60 mmol) was dissolved in DCM (35 mL), cooled to −78° C., stirred for 5 minutes followed by addition of a solution of dimethylsulfoxide (870 µL, 12.3 mmol) in DCM (2.5 mL). After stirring for 5 minutes 7 (1.05 g, 3.15 mmol) in dichloromethane (20 mL) was added followed by triethylamine (2.37 mL, 17.0 mmol). The reaction was slowly warmed to room temperature. DCM and H₂O were added, the aqueous layer seperated and extracted 2× with DCM. The DCM portions were combined, filtered through Na₂SO₄, and concentrated to give 8 in 95% yield.

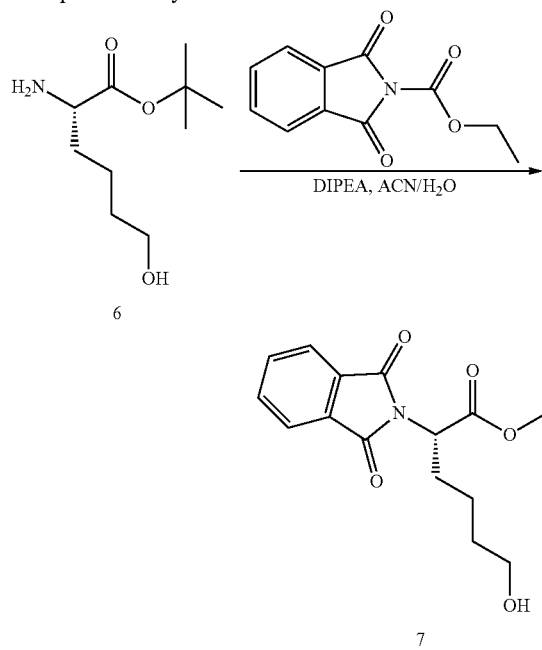

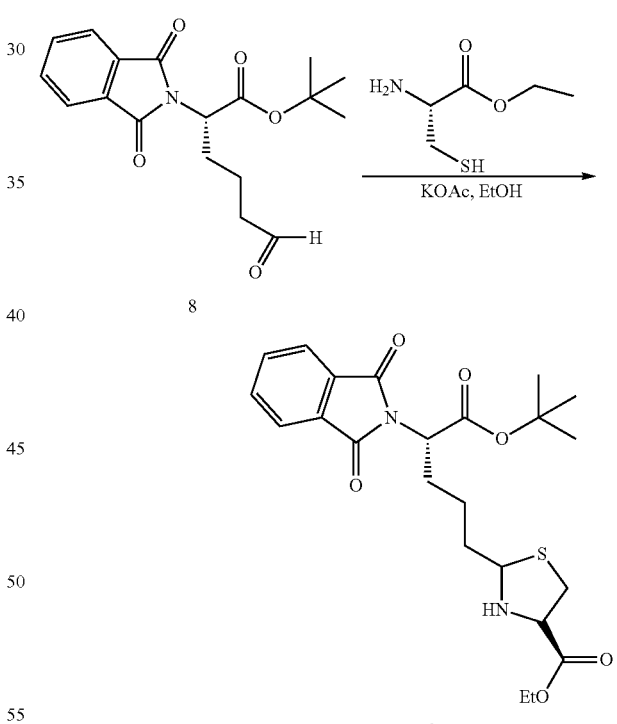

To 6 (42 mg, 0.21 mmol) in ACN (2 mL) carbethoxyphthalimide (50 mg, 0.23 mmol) was added with DIPEA (40 µL, 0.23 mmol) and stirred at room temperature for 2 hours. H₂O (1 mL) was added and stirred for an additional 10 minutes. The ACN was evaporated off and DCM and 10% citric acid were added. The aqueous layer was seperated and extracted 3× with DCM, the DCM portions were combined, dried with Na₂SO₄, and concentrated to give 7 in 95% yield.

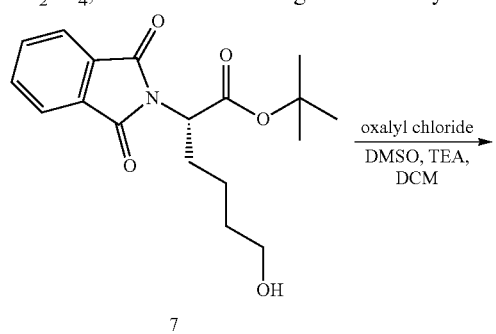

L-cysteine ethyl ester hydrochloride (643 mg, 3.5 mmol) and potassium acetate (343 mg, 3.5 mmol) were dissolved in stirring EtOH (13 mL), and cooled to 0° C. in an ice water bath. Compound 8 was dissolved in EtOH (13 mL) and added. The reaction was stirred at 0° C. for 4 hours, LCMS confirmed the conversion of 8 into two diastereomeric products. The reaction was filtered, EtOH evaporated, redissolved in DCM and washed with brine, dried with MgSO₄ and concentrated to give a 1:1 mixture of diastereomers 9 in quantitative yield.

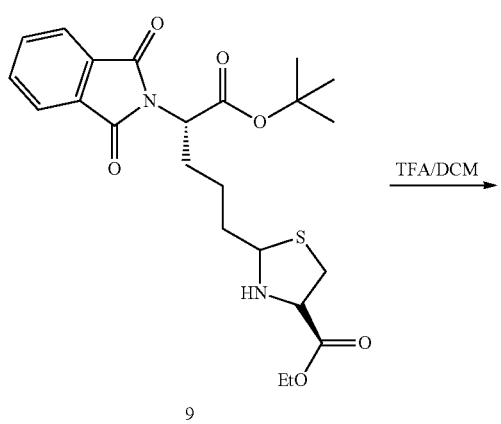

9

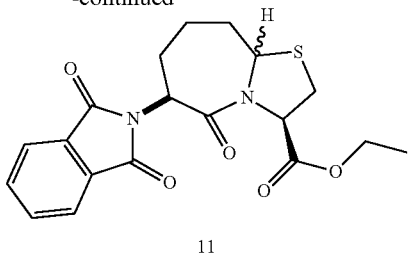

11

To a stirred solution of 10 (675 mg, 1.67 mmol) in THF (20 mL), EEDQ (619 mg, 2.50 mmol) was added. Stirred at room temperature for 2 days. The THF was removed under reduced pressure, the product redissoved in EtOAc. The organic layer was washed with 0.5 N HCl, 0.5% NaHCO$_3$, H$_2$O, brine. The EtOAc solution was dried with MgSO$_4$ and concentrated. The product was purified via reverse phase HPLC 10-70% ACN in H$_2$O to give two diastereomers 11, 20% yield for diastereomer 1 and 18% yield for diastereomer 2.

Example 2

2-[tert-butoxycarbonyl-(1H-pyrrol-2-ylmethyl)-amino]-propionic acid

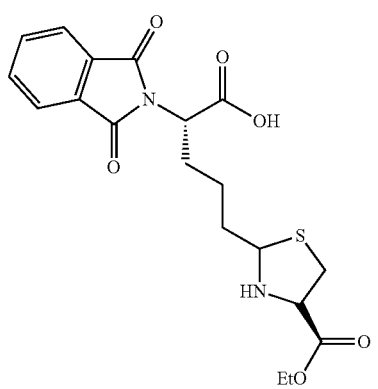

10

The diastereomers were redissolved in 1:1 TFA:DCM (10 mL) and stirred for 1 hour at room temperature. LCMS showed complete conversion to 10. The reaction was concentrated to give 10 in 95% yield for the two diastereomers.

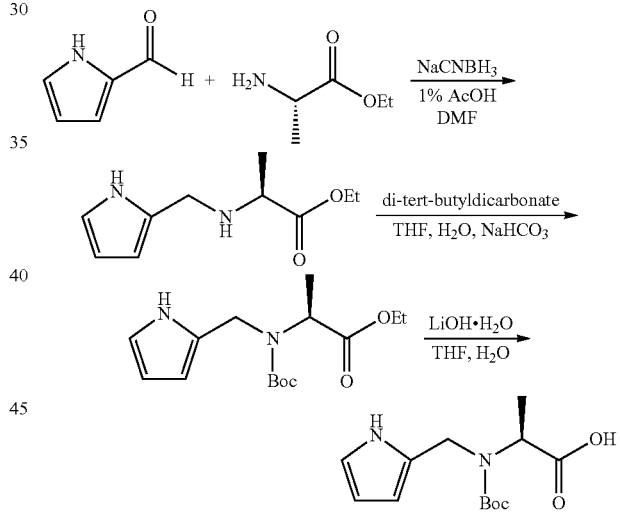

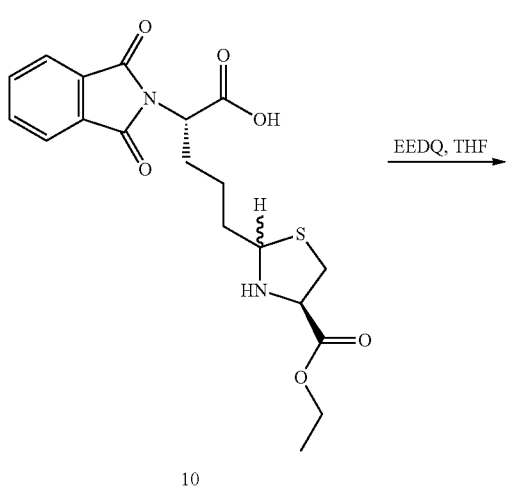

10

Alanine ethyl ester (5 g, 32.5 mmol), pyrrole-2-carboxaldehyde (3.1 g, 32.5 mmol), sodium cyanoborohydride (2.04 g, 32.5 mmol) and AcOH (1%) were mixed in DMF and stirred overnight. The reaction was quenched with H$_2$O, and DMF was evaporated. The mixture was diluted with EtOAc, washed by 0.1N NaOH, dried and concentrated to yield product 2.5 g. The resulting ester (2.5 g, 12.8 mmol), di-tert-butyldicarbonate (3.06 g, 14 mmol) were mixed in THF, H$_2$O with NaHCO$_3$ and stirred overnight. THF was evaporated, and the mixture was diluted with EtOAc, washed by 1N NaOH, sat. NH$_4$Cl and brine. After dried, the mixture was concentrated to yield the Boc-protected ester 3.3 g. The Boc-protected ester (1.67 g, 5.6 mol), lithium hydroxide mono hydrate (284 mg, 6.77 mmol) were mixed in THF and H$_2$O at 0° C. THF was vacuumed off, and the solution was acidified by dilute H$_2$SO$_4$, extracted by EtOAc twice. Organic layers were combined, dried and evaporated.

Example 3

Tetrahydropyranylglycine

Tetrahydropyranylglycine is available from NovaBiochem, or synthezed according to the literature: Ghosh, A. K.; Thompson, W. J.; holloway, M. K.; McKee, S. P.; Duong, T. T.; Lee, H.Y.; Munson, P. M.; Smith, A. M.; Wai, J. M; Darke, P. L.; Zugay, J. A.; Emini, E. A.; Schleife, W. A.; Huff, J. R.; Anderson, P. S. *J. Med. Chem.,* 1993, 36, 2300-2310.

Example 4

Piperidinylglycine

Piperidinylglycine was synthesized according to the literature: Shieh, W—C.; Xue, S.; Reel, N.; Wu, R.; Fitt, J.; Repic, O. *Tetrahedron: Asymmetry,* 2001, 12, 2421-2425.

Example 5

4,4-difluorocyclohexylglycine 4,4-difluorocyclohexylglycine was made according to the procedures described in US 2003/0216325.

Example 6

Boc (S)-2-amino-2-(4-hydroxycyclohexyl)acetic acid

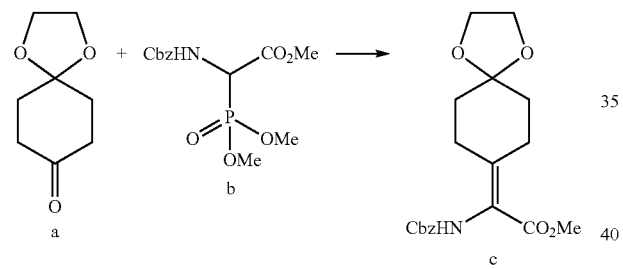

Following the procedure of Sheih, (*Tetrahedron: Asymmetry,* 2001, 12, 2421-2425), a solution of ketone a (8.4 g) and EtOAc (30 mL) was added to a solution of N-Cbz-phosphonoglycine methyl ester b, TMG (4.5 mL) and EtOAc (30 mL). The solution was maintained at rt for 48 h, then washed with 1N HCl (3×50 mL), brine (1×50 mL) dried (Na$_2$SO$_4$), filtered, and concentrated. The residue was adsorbed onto Celite, and purified by chromatography, then further purified by re-crystallization from EtOAc/hexanes to afford 5.2 g of product c.

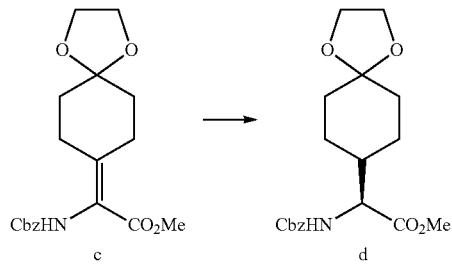 [SMILES: COC(=O)C(NC(=O)OCc1ccccc1)=C1CCC2(CC1)OCCO2 ; COC(=O)[C@@H](NC(=O)OCc1ccccc1)C1CCC2(CC1)OCCO2]

Following the procedure of Sheih, (*Tetrahedron: Asymmetry,* 2001, 12, 2421-2425), a solution of eneamide c (5.0 g), (S,S)-Me-BPE-Rh(I) (1.5 g, Strem Chemicals, Newburyport, Mass.), and MeOH (100 mL) was shaken virgorously under 70 psi of H$_2$ for 48 h. The solvent was removed under reduced pressure. The residue was taken up in EtOAc, and filtered through SiO$_2$ with more EtOAc. The solvent was removed under reduced pressure to afford 4.0 g of product d as a colorless solid.

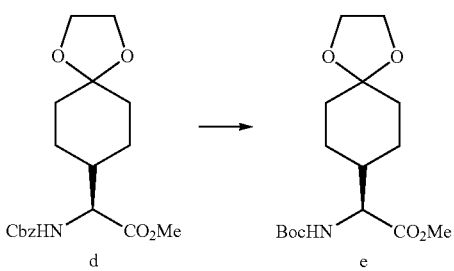 [SMILES: COC(=O)[C@@H](NC(=O)OCc1ccccc1)C1CCC2(CC1)OCCO2 ; COC(=O)[C@@H](NC(=O)OC(C)(C)C)C1CCC2(CC1)OCCO2]

A mixture of Cbz-carbamate d, (4.0 g) Boc$_2$O, (2.9 g), 20% Pd(OH)$_2$.C (1.0 g) and MeOH (30 mL) was maintained under an atmosphear of H$_2$ for 6 h. The mixture was filtered through Celite with MeOH. The solvent was removed under reduced pressure to afford 4.5 g of residue e, which was taken on directly.

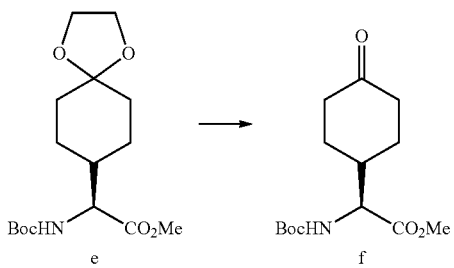 [SMILES: COC(=O)[C@@H](NC(=O)OC(C)(C)C)C1CCC2(CC1)OCCO2 ; COC(=O)[C@@H](NC(=O)OC(C)(C)C)C1CCC(=O)CC1]

The residue e from above was dissolved in H$_2$O (10 mL), AcOH (30 mL), THF (5 mL), and dichloroacetic acid (3 mL) and maintained at rt overnight. Water (5 mL) was added and the solution and maintaned until hyrolysis was complete, as monitored by HPLC-MS. Solid Na$_2$CO$_3$ was added cautiously until gas evolution ceased, the mixture was diluted with aq NaHCO$_3$, and extracted with 10% EtOAc/DCM. The combined organic phases were washed once with brine, dried (Na$_2$SO$_4$), filtered, and concentrated. The residue was purified by chromatography to afford 2.9 g of product f.

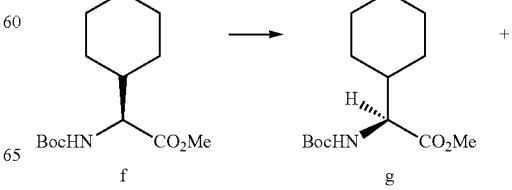

-continued

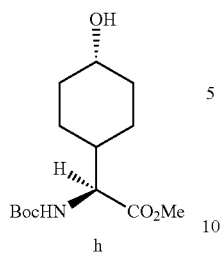

A mixture of ketone f (1.5 g) MeOH (50 ml) was treated with NaBH₄ (290 mg) at 0° C. for 20 min. The mixture was acidifed to ~pH1 with 10% aq citric acid and the MeOH was removed under reduced pressure. The residue was diluted with water and extraced with 20% EtOAc/DCM. The combined organic phases were washed once with brine, dried (Na₂SO₄), filtered, and concentrated. The residue was purified by chromatography to afford 1.17 g of product g and 0.23 g of product h.

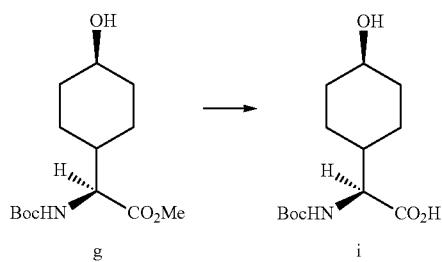

A mixture of ester g (1.17 g) LiOH.H2O (160 mg), THF (3 mL) and water (4.5 mL) was stirred vigorously at rt overnight. The mixture was diluted with brine and exaustivly extraced with EtOAc. The combined organic phases were washed once with brine, dried (Na₂SO₄), filtered, and concentrated to afford acid i (525 mg).

Example 7

N-Boc-N-cyclopropylmethyl-L-alanine

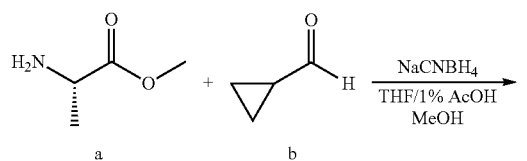

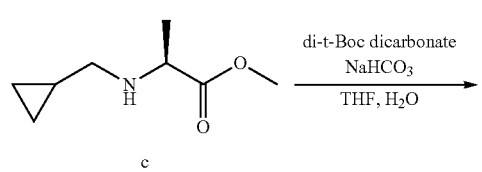

-continued

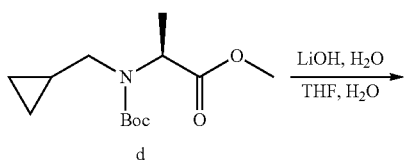

L-alanine methyl ester hydrochloride a (5 g, 35.8 mmol) and cyclopropanecarboxaldehyde b (2.67 ml, 35.8 mmol) were suspended in 50 ml THF w/1% AcOH. Addition of 5 ml of CH₃OH made the cloudy solution turned to clear. NaCNBH₄ (2.25 g, 35.8 mmol) was added and the reaction mixture stirred overnight. The reaction was quenched by addition of 1N aq. NaOH, extracted by EtOAc twice, organic layers were dried over Na₂SO₄ and concentrated to dryness. The crude material was purified by chromatography using 30% EtOAc/hexane (stained by ninhydrin) to obtain the compound c (1 g, 18%).

The compound c (1 g, 6.37 mmol) and di-t-bocdicarbonate (2.1 g, 9.55 mmol) were diluted in THF (20 ml) and H₂O (20 ml), NaHCO₃ (1.3 g, 15.9 mmol) was added. The reaction mixture stirred overnight for completion. THF was removed under reduced pressure, and the aqueous layer was extracted by EtOAc 3 times. Combined organic layers were washed by 1N NaOH, sat, NH₄Cl followed by brine, the concentrated to dryness. The Boc-protected compound d (1.39 g, 5.40 mmol) was stirred with LiOH.H₂O (1.14 g, 27 mmol) in THF (20 ml) and H₂O (20 ml) overnight at room temperature. THF was stripped off, and the aqueous layer was adjusted to pH=4 by adding 10% citric acid, then extracted by EtOAc 3 times. Combined organic layers were washed by brine and concentrated. The crude was purified by reverse phase C-18 column eluted by 0%-50% acetonitrile/H₂O to give pure compound e as a white solid (794 mg).

Example 8

Acid Fluoride Coupling Procedure

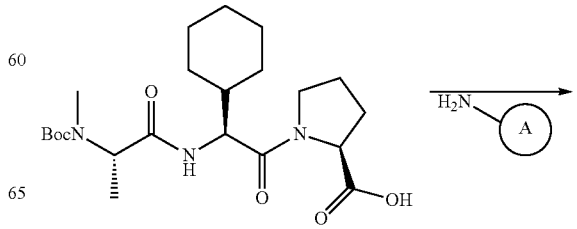

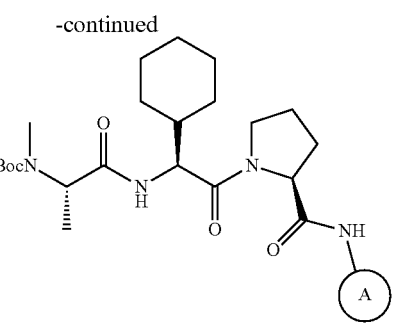

A solution of Boc-MeAla-Chg-Pro-OH (2.3 mmol) and pyridine (6.9 umol) in anhydrous dichloromethane (23 ml) was cooled to 0° C. and cyanuric fluoride (2.3 mmol) added dropwise over 30 sec. The mixture was stirred at 0° C. for 15 min, at ambient temperature for 5 hr, and then quenched with water. The mixture was extracted three times with dichloromethane (total 100 ml), and the combined organic phases washed with brine and dried over anhydrous sodium sulfate. Filtration and concentration in vacuo yielded the peptide acid fluoride as a clear, colorless oil used directly without further purification.

A solution of the crude acid fluoride (0.50 mmol) and pyridine (1.5 mmol) in dichloromethane (2.5 ml) was added to the solid amine (0.50 mmol), and the resulting mixture stirred either at ambient temperature or at 50° C. (sealed vessel). The mixture was poured into aqueous sodium bicarbonate and the extracted three times with dichloromethane (total 100 ml). The combined organic phases were washed with brine, dried over anhydrous sodium sulfate, filtered and concentrated in vacuo. The crude peptide amide was used directly without further purification.

Example 9

Compound 3

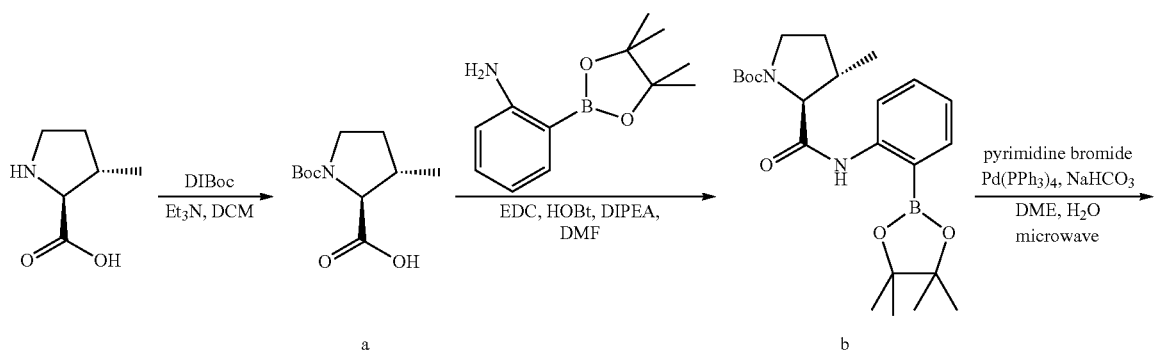

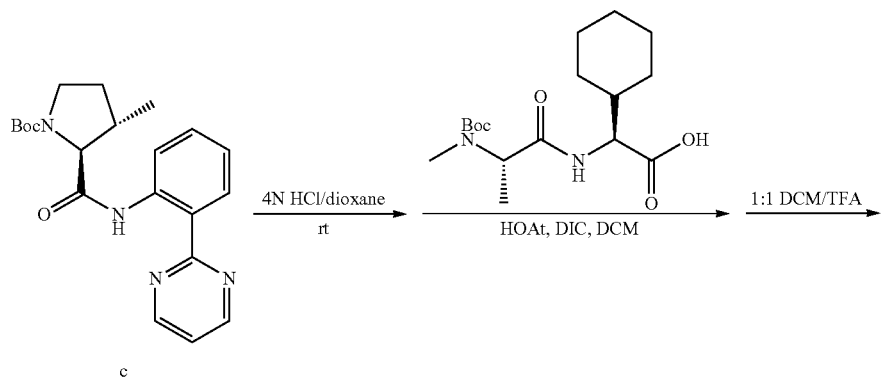

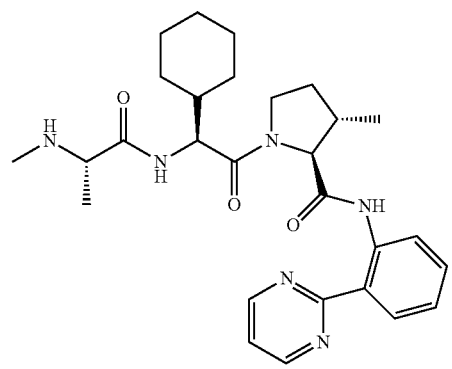

The methyl Pro-OH (0.25 g, 0.0019 mol) was suspended in Methylene chloride (11 mL, 0.18 mol), and treated with Triethylamine (0.81 mL, 0.0058 mol), the reaction mixture was cooling to 0 degree and Di-tert-Butyldicarbonate (0.84 g, 0.0039 mol) was added, the reaction was allow to warm to room temperature and stirred overnight. 10% of citric acid solution was added to quench the reaction. The aqueous layer was extracted by DCM three times. Organic layers were combined and dried by sodium sulfate. The solvent was removed under reduced pressure. The crude compound a was used without further purification.

2-(4,4,5,5-tetramethyl-1,3,2-dioxaborolan-2-yl)aniline (0.84 g, 0.0038 mol; Aldrich) was dissolved in DMF and treated with the compound a (0.44 g, 0.0019 mol), N-(3-dimethylaminopropyl)-N'-ethylcarbodiimide hydrochloride, 1-hydroxybenzotriazole and DIPEA. The reaction was heated to 50° C. overnight and then quenched with sat. NaHCO₃, extracted with 3× EtOAc, dried, concentrated and purified by ISCO chromatography (0-50% EA/Hex). The major product was tested by NMR, which indicated desired product. Yield (0.4 g, 50%).

2-pyrimidine bromide (0.17 g, 0.0010 mol; Aldrich), the compound b (0.4 g, 0.0009 mol), tetrakis(triphenylphosphine)palladium(0) (0.054 g, 0.000046 mol), sodium bicarbonate (0.39 g, 0.0046 mol) were suspended in dimethoxyethane and water in a 40 ml microwave vessel, degased and filled under an N₂ atmosphere. The process was repeated 2× and then microwaved at 150° C. for 20 min at which point the reaction was complete.

The reaction mixture was diluted with CH₂Cl₂, washed with 1N NaOH, extracted by CH₂Cl₂ 2×, dried, concentrated, and purified by ISCO chromatography (40 g column, 0-50% EtOAc/Hexane). Yield (0.21 g, 60%).

The compound c was treated with 4 N HCl/1,4-dioxane. The reaction was carried out for 30 minutes and concentrated in vacuo. The crude was used in next step without further purification.

Deprotected compound c (200 mg, 0.0007 mol) was diluted with DCM, and treated with the dipeptide (270 mg, 0.00080 mol), N,N'-diisopropylcarbodiimide (0.17 mL, 0.0011 mol) and 1-hydroxy-7-azabenzotriazole (140 mg, 0.0011 mol). The reaction was stirred at room temperature for 1 hr. LCMS showed no SM left, major DP. Diluted with DCM, washed by water, organic layer was dried, concentrated and purified by ISCO chromatograpy (50-80% EA/Hex). Yield (0.2 g, 50%). Treatment with 1:1 TFA and DCM at room temperature for 30 minutes and concentrated to dry to give crude compound 3. 124 mg of pure material was obtained.

Example 10

Compound 4

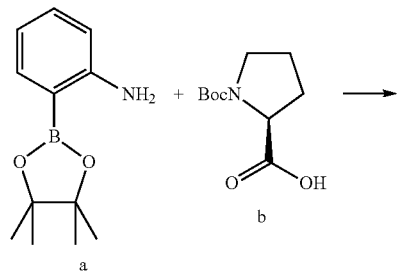

b

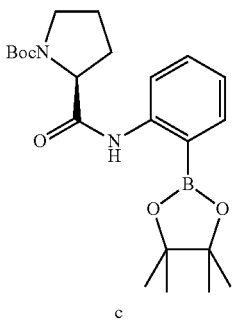

c

To 2-aminophenylboronic acid pinacol ester a (3.0 g, 0.014 mol) and N-Boc-L-proline b (3.0 g, 0.014 mol) in N,N-dimethylformamide (15 mL) was added N-(3-dimethylaminopropyl)-N'-ethylcarbodiimide hydrochloride (2.6 g, 0.014 mol), 1-hydrozybenzotriazole (1.9 g, 0.014 mol), and then N,N-diisopropylethylamine (2.4 mL, 0.014 mol). The reaction was heated to 60° C., stirred several days, cooled to room temperature, and then quenched by the addition of a saturated aqueous solution of sodium bicarbonate. The aqueous layer was extracted with EtOAc and the combined organic layers were dried over MgSO₄, filtered, and concentrated. The crude residue was purified by ISCO chromatography (80 g column, 0 to 80% EtOAc/Hexanes) to give (S)-tert-butyl 2-(2-(4,4,5,5-tetramethyl-1,3,2-dioxaborolan-2-yl)phenylcarbamoyl) pyrrolidine-1-carboxylate c (2.87 g, 49%).

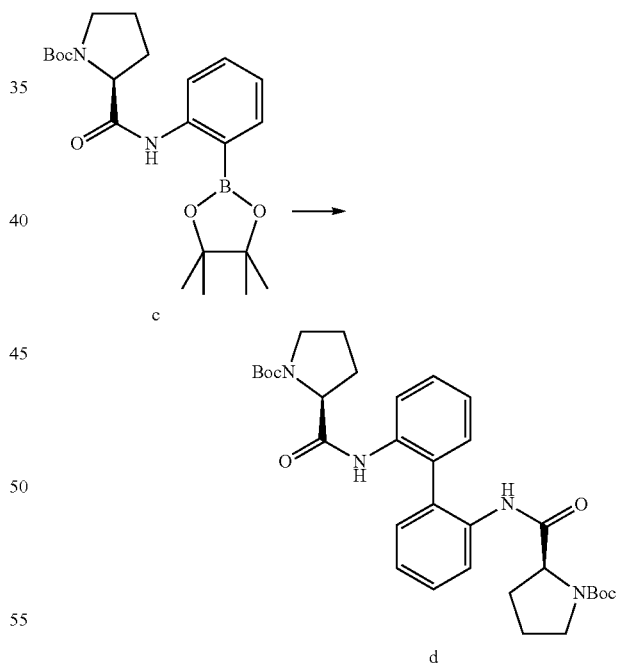

(S)-tert-butyl2-(2-(4,4,5,5-tetramethyl-1,3,2-dioxaborolan-2-yl)phenylcarbamoyl)pyrrolidine-1-carboxylate c (0.50 g, 0.001 mol), 1-bromo-2-fluorobenzene (0.18 g, 0.001 mol), potassium carbonate (0.41 g, 0.003 mol), and dichlorobis(triphenylphosphine)-palladium (II) (catalytic) were combined in dry 1,2-dimethoxyethane (30 mL). Nitrogen was bubbled through the reaction mixture for 15 minutes. The reaction was heated to 80° C. and stirred overnight. The reaction mixture was cooled to room temperature, diluted with EtOAc, filtered through celite, and concentrated. The crude residue was purified by ISCO chromatography (40 g column, 0 to 100% EtOAc/Hexanes) to give (2S,2'S)-tert-butyl-2,2'-(biphenyl-2,2'-diylbis(azanediyl))bis(oxomethylene)dipyrrolidine-1-carboxylate d (0.140 g, 24%). LC/MS: mw 578.70; M+H⁺=579.5.

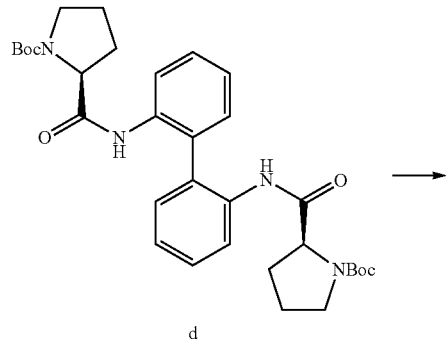

d

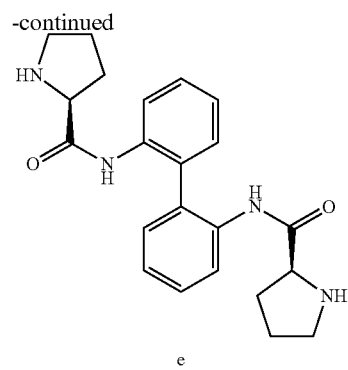

e (2S,2'S)-tert-butyl-2,2'-(biphenyl-2,2'-diylbis(azanediyl))bis(oxomethylene)dipyrrolidine-1-carboxylate d (0.140 g, 0.24 mmol) was suspended in a solution of 4M HCl/dioxane and stirred at room temperature for 4 h until LCMS indicated complete deprotection. The reaction mixture was concentrated to give (2S,2'S)—N,N'-(biphenyl-2,2'-diyl)dipyrrolidine-2-carboxamide e (0.09 g, 100%). LC/MS: mw 378.47; M+H⁺=379.2.

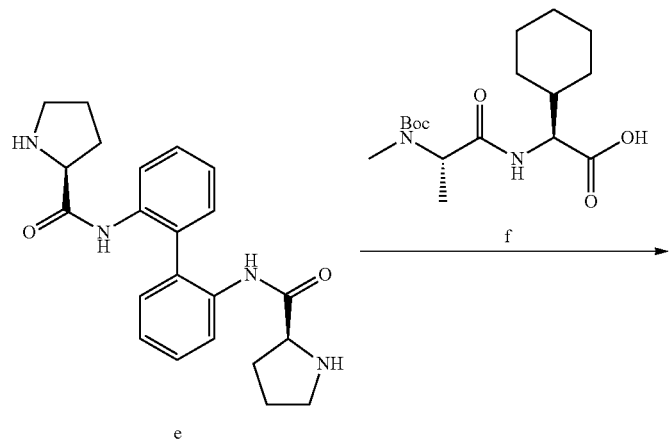

e

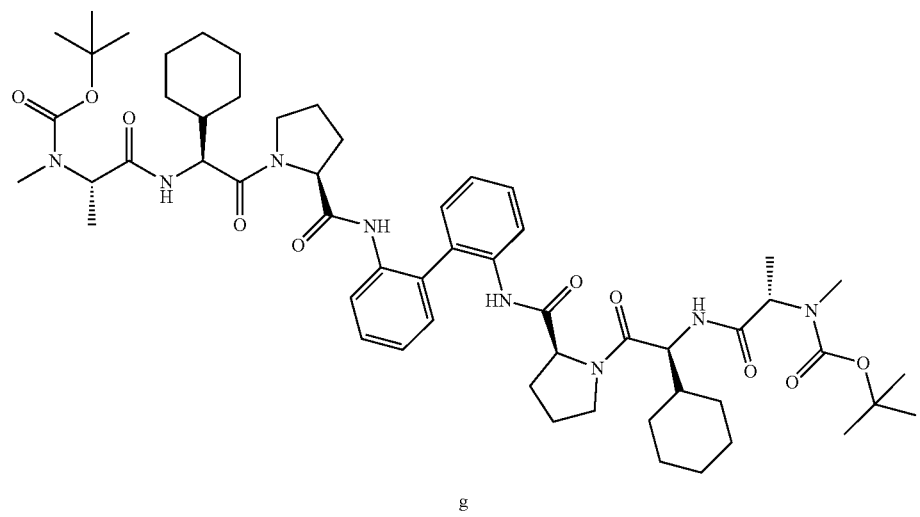

g

To (2S,2'S)—N,N'-(biphenyl-2,2'-diyl)dipyrrolidine-2-carboxamide e (0.09 g, 0.24 mmol) was added CH$_2$Cl$_2$ (10 mL) and cooled in an ice bath. To this mixture was added N,N-diisopropylethylamine (0.16 mL, 0.96 mmol), HOAt (0.07 g, 0.58 mmol), allowed to stir at room temperature for 5 minutes, and then added DIC (0.09 mL, 0.58 mmol). The mixture was then allowed to stir at room temperature overnight, diluted with EtOAc (25 mL), and then quenched by the addition of a saturated aqueous solution of sodium bicarbonate. The aqueous layer was extracted with EtOAc and the combined organic layers were dried over MgSO$_4$, filtered, and concentrated. The crude residue was purified by ISCO chromatography (12 g column, 0 to 100% EtOAc/Hexanes) to give tert-butyl (2S,2'S)-1,1'-(1S, 1'S)-2,2'4(2S,2'S)-2,2'-(biphenyl-2,2' diylbis(azanediyl))bis(oxo-methylene)bis(pyrrolidine-2,1-diyl))bis(1-cyclohexyl-2-oxoethane-2,1diyl)bis(azanediyl)bis(1-oxopropane-2,1-diyl)bis(methylcarbamate) g (0.141 g, 57%). LC/MS: mw 1027.30; M+H$^+$=1027.8.

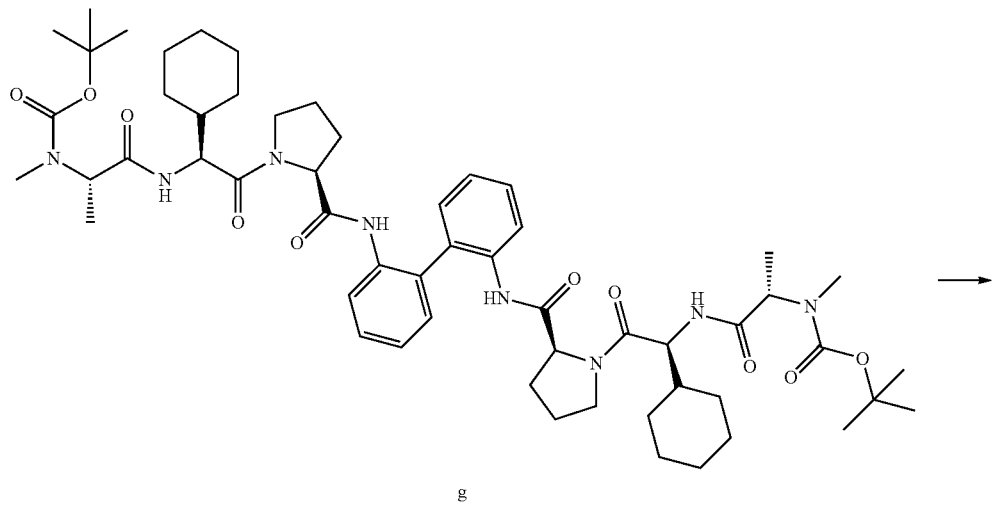

g

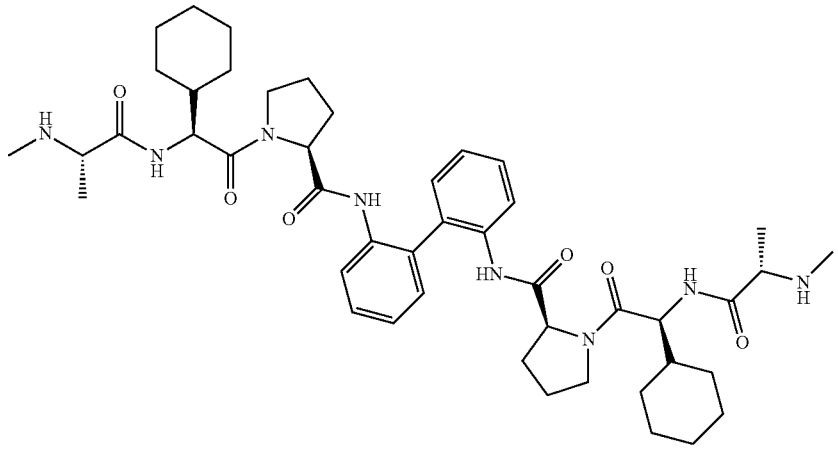

4

To tert-butyl-(2S,2'S)-1,1'-((1S,1'S)-2,2'-((2S,2'S)-2,2'-(biphenyl-2,2'-diylbis(azanediyl)) bis(oxo-methylene)bis(pyrrolidine-2,1-diyl))bis(1-cyclohexyl-2-oxoethane-2,1-diyl) bis(azanediyl)bis(1-oxopropane-2,1-diyl)bis(methylcarbamate) g (0.141 g, 0.14 mmol) was added CH$_2$Cl$_2$ (2 mL) and TFA (2 mL), allowed to stir for 2 h, and concentrated. The residue was purified by HPLC to give compound 4 (S,S,2S,2'S)—N,N'-(biphenyl-2,2'-diyl)bis(1-((S)-2-cyclohexyl-2-((S)-2-(methylamino) -propanamido)acetyl)pyrrolidine-2-carboxamide) (0.015 g, 14%). LC/MS: mw 827.07; M+H$^+$=827.5.

Example 11

Compound 8

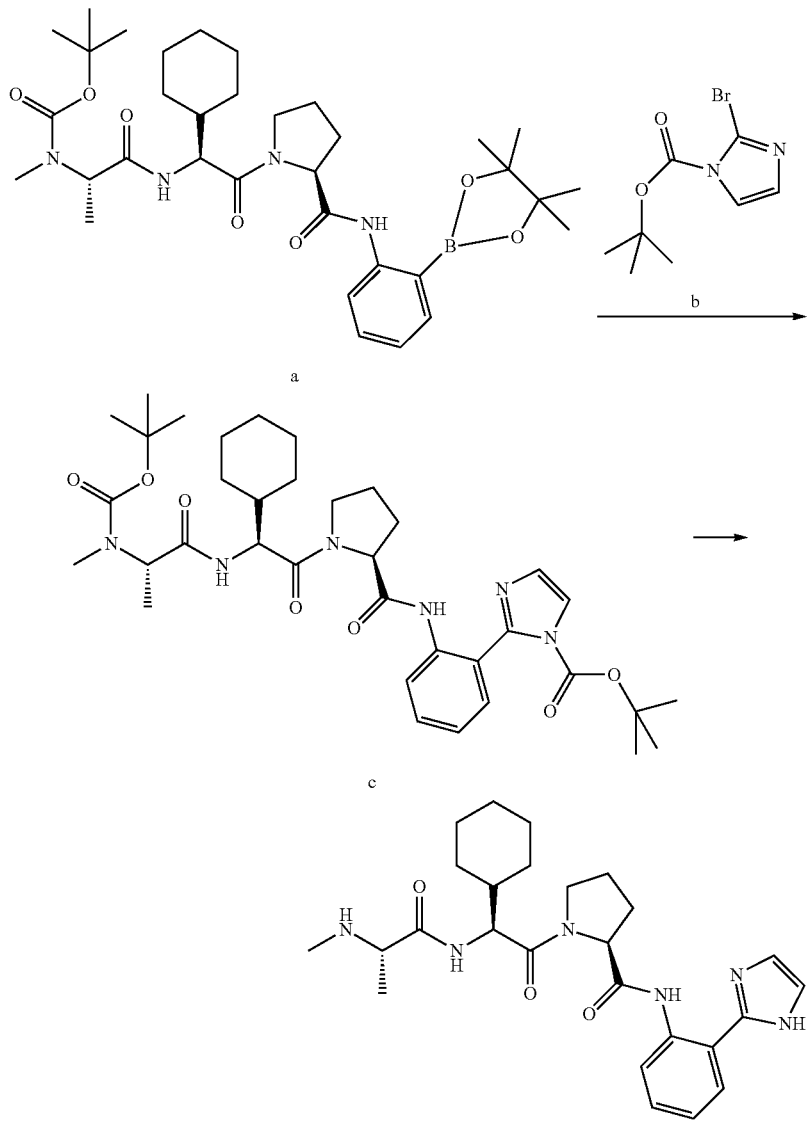

Peptide a (0.34 g, 0.00053 mol), b (0.26 g, 0.0011 mol), tetrakis(triphenylphosphine)palladium(0) (0.031 g, 0.000026 mol) and sodium bicarbonate (0.22 g, 0.0026 mol) were suspended in dimethoxyethane and water in a 40 ml microwave vessel, degased and filled under an $N_2$ atmosphere. The process was repeated 2x. Microwaved at 150° C. for 20 min at which point the reaction was complete. LCMS showed desired product peak. The reaction mixture was diluted with $CH_2Cl_2$, washed with 1N NaOH, extracted by $CH_2Cl_2$ 2x, dried and concentrated. Purified by ISCO chromatography (40 g column, 0-50% EtOAc/Hexane). Intermediate c was reacted with TFA in methylenechloride for 30 mins and concentrated. LCMS showed 4 major peaks, DP peak at 1.32 min. The compound was dissolved in DMF, purified by prep HPLC (5%-30% 20 min, flow rate was reduced to 30 ml/min) and lyophilized to give 22 mg of compound 8 as a white loose powder.

Example 12

IAP Inhibition Assays

In the following experiments was used a chimeric BIR domain referred to as MLXBIR3SG in which 11 of 110 residues correspond to those found in XIAP-BIR3, while the remainder correspond to ML-IAP-BIR. The chimeric protein MLXBIR3SG was shown to bind and inhibit caspase-9 significantly better than either of the native BIR domains, but bound Smac-based peptides and mature Smac with affinities similar to those of native ML-IAP-BIR. The improved caspase-9 inhibition of the chimeric BIR domain MLXBIR3SG has been correlated with increased inhibition of doxorubicin-induced apoptosis when transfected into MCF7 cells.

MLXBIR3SG Sequence:

(SEQ ID NO.: 1)
MGSSHHHHHHSSGLVPRGSHMLETEEEEEGAGATLSRGPAFPGMGSEE

LRLASFYDWPLTAEVPPELLAAAGFFHTGHQDKVRCFFCYGGLQSWKRG

DDPWTEHAKWFPGCQFLLRSKGQEYINNIHLTHSL

TR-FRET Peptide Binding Assay

Time-Resolved Fluorescence Resonance Energy Transfer competition experiments were performed on the Wallac Victor2 Multilabeled Counter Reader (Perkin Elmer Life and Analytical Sciences, Inc.) according to the procedures of Kolb et al (Journal of Biomolecular Screening, 1996, 1(4): 203). A reagent cocktail containing 300 nM his-tagged MLXBIR3SG; 200 nM biotinylated SMAC peptide (AVPI); 5 µg/mL anti-his allophycocyanin (XL665) (CISBio International); and 200 ng/mL streptavidin-europium (Perkin Elmer) was prepared in reagent buffer (50 mM Tris [pH 7.2], 120 mM NaCl, 0.1% bovine globulins, 5 mM DTT and 0.05% octylglucoside). (Alternatively, this cocktail can be made using europium-labeled anti-His (Perkin Elmer) and streptavidin-allophycocyanin (Perkin Elmer) at concentrations of 6.5 nM and 25 nM, respectively). The reagent cocktail was incubated at room temperature for 30 minutes. After incubation, the cocktail was added to 1:3 serial dilutions of an antagonist compound (starting concentration of 50 µM) in 384-well black FIA plates (Greiner Bio-One, Inc.). After a 90 minute incubation at room temperature, the fluorescence was read with filters for the excitation of europium (340 nm) and for the emission wavelengths of europium (615 nm) and a allophycocyanin (665 nm). Antagonist data were calculated as a ratio of the emission signal of allophycocyanin at 665 nm to that of the emission of europium at 615 nm (these ratios were multiplied by a factor of 10,000 for ease of data manipulation). The resulting values were plotted as a function of antagonist concentration and fit to a 4-parameter equation using Kaleidograph software (Synergy Software, Reading, Pa.).

Indications of antagonist potency were determined from the $IC_{50}$ values. Compounds of the invention where found to have IAP inhibitory activity which was demonstrated in this assay.

Fluorescence Polarization Peptide Binding Assay

Polarization experiments were performed on an Analyst HT 96-384 (Molecular Devices Corp.) according to the procedure of Keating, S. M., Marsters, J, Beresini, M., Ladner, C., Zioncheck, K., Clark, K., Arellano, F., and Bodary., S.(2000) in *Proceedings of SPIE: In Vitro Diagnostic Instrumentation* (Cohn, G. E., Ed.) pp 128-137, Bellingham, Wash. Samples for fluorescence polarization affinity measurements were prepared by addition of 1:2 serial dilutions starting at a final concentration of 5 µM of MLXBIR3SG in polarization buffer (50 mM Tris [pH 7.2], 120 mM NaCl, 1% bovine globulins 5 mM DTT and 0.05% octylglucoside) to 5-carboxyflourescein-conjugated AVPdi-Phe-$NH_2$ (AVP-diPhe-FAM) at 5 nM final concentration.

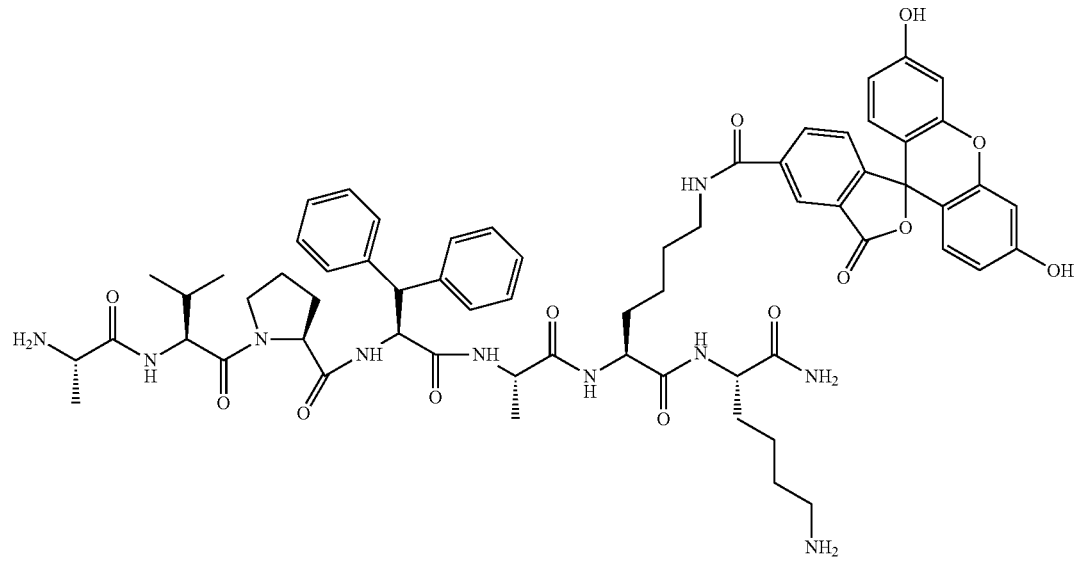

AVP-diPhe-FAM probe

The reactions were read after an incubation time of 10 minutes at room temperature with standard cut-off filters for the fluorescein fluorophore($\lambda_{ex}$=485 nm; $\lambda_{em}$=530 nm) in 96-well black HE96 plates (Molecular Devices Corp.). Fluorescence values were plotted as a function of the protein concentration, and the IC50s were obtained by fitting the data to a 4-parameter equation using Kaleidograph software (Synergy software, Reading, Pa.). Competition experiments were performed by addition of the MLXBIR3SG at 30 nM to wells containing 5 nM of the AVP-diPhe-FAM probe as well as 1:3 serial dilutions of antagonist compounds starting at a concentration of 300 µM in the polarization buffer. Samples were read after a 10-minute incubation. Fluorescence polarization values were plotted as a function of the antagonist concentration, and the $IC_{50}$ values were obtained by fitting the data to a 4-parameter equation using Kaleidograph software (Synergy software, Reading, Pa.) Inhibition constants ($K_i$) for the antagonists were determined from the $IC_{50}$ values. Compounds of the invention where found to have IAP inhibitory activity which was demonstrated in this assay.

We claim:

1. A compound of formula I:

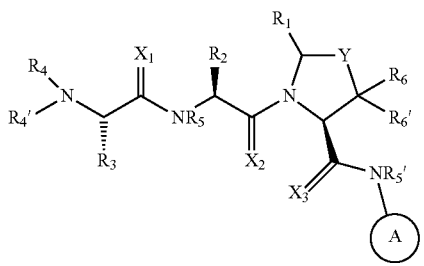

wherein
- $X_1$, $X_2$ and $X_3$ are each independently O or S;
- Y is $CH_2$;
- A is a 6-member aromatic ring or a 6-member heteroaromatic ring comprising 1 to 4 heteroatoms, wherein the aromatic ring and heteroaromatic ring are each substituted with hydroxyl, halogen, alkoxy, aryl, or a heterocycle; wherein each aryl and heterocycle substituent is optionally substituted with hydroxyl, halogen, mercapto, carboxyl, alkyl, alkoxy, haloalkyl, amino, nitro, cyano, cycloalkyl, aryl or a heterocycle;
- $R_1$ is H;
- $R_2$ is alkyl or cycloalkyl, wherein each alkyl and cycloalkyl is optionally substituted with hydroxyl, mercapto, halogen, amino, carboxyl, alkyl, haloalkyl, alkoxy or alkylthio;
- $R_3$ is H or alkyl;
- $R_4$ and $R_4$' are each independently H or alkyl, with the proviso that when one of $R_4$ and $R_4$' is H, the other is alkyl;
- $R_5$ and $R_5$' are each independently H or alkyl; and
- $R_6$ and $R_6$' are each independently H or alkyl;

or a pharmaceutically acceptable salt thereof.

2. The compound of claim 1, wherein ring A has the formula IIa:

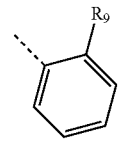

wherein $R_9$ is hydroxyl, halogen, alkoxy, aryl or a heterocycle; wherein each aryl and heterocycle is optionally substituted with halogen or alkoxy.

3. The compound of claim 1, wherein $R_2$ is isopropyl, t-butyl, or cyclohexyl.

4. The compound of claim 1, wherein $R_3$ is methyl.

5. The compound of claim 1, wherein $R_4$ is methyl, and $R_4$' is H.

6. The compound of claim 1, wherein $R_5$ and $R_5$' are independently H or methyl.

7. The compound of claim 1, wherein $R_6$ and $R_6$' are independently H or methyl.

8. The compound of claim 1, wherein $X_1$, $X_2$ and $X_3$ are each O.

9. The compound of claim 1, wherein $R_2$ is isopropyl, t-butyl, or cyclohexyl; $R_3$ is methyl; $R_4$ is methyl; $R_4'$ is H; $R_5$ and $R_5'$ are each independently H or methyl; and $X_1$, $X_2$ and $X_3$ are each O.
10. A compound selected from the group consisting of:
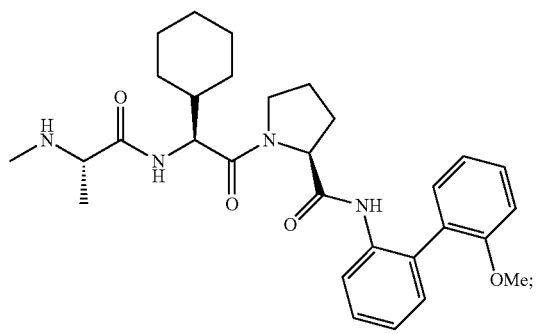
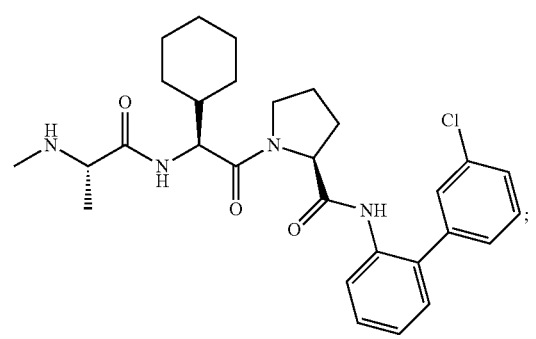
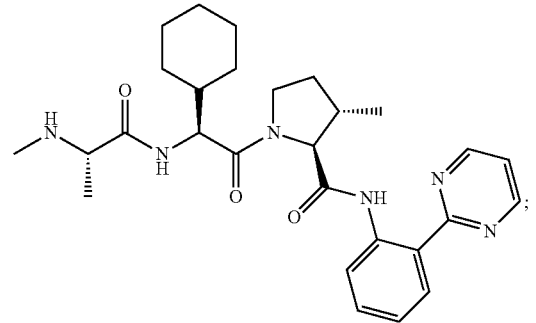
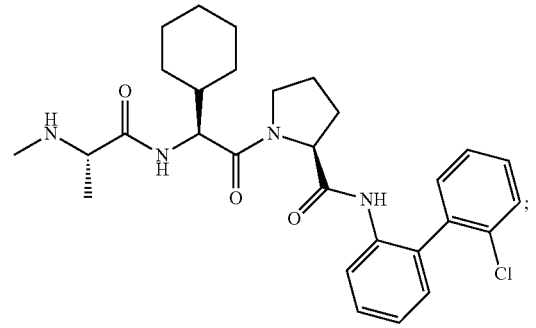
-continued
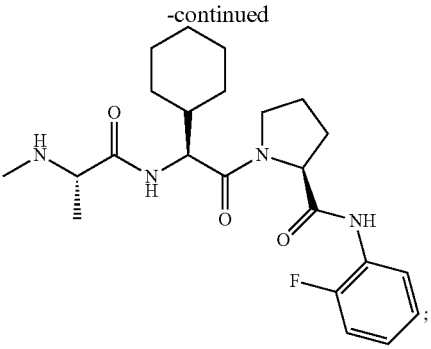
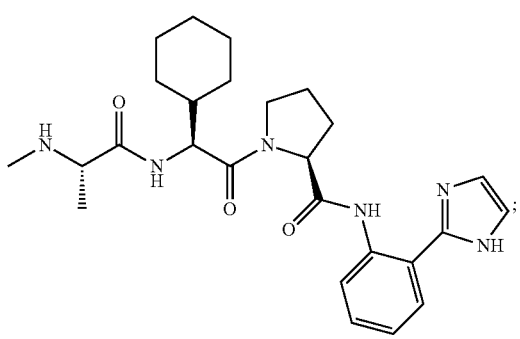
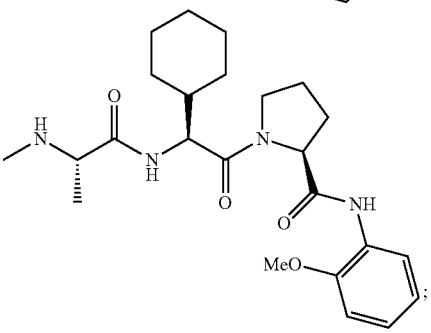
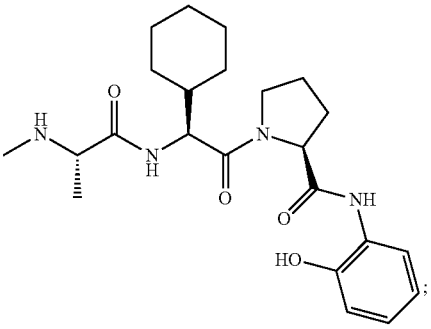
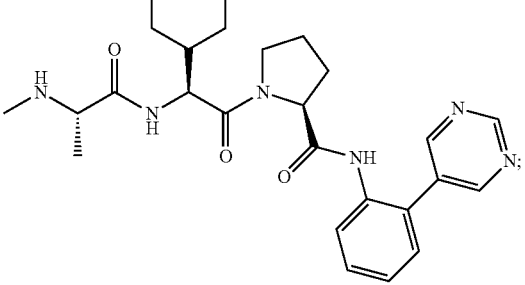

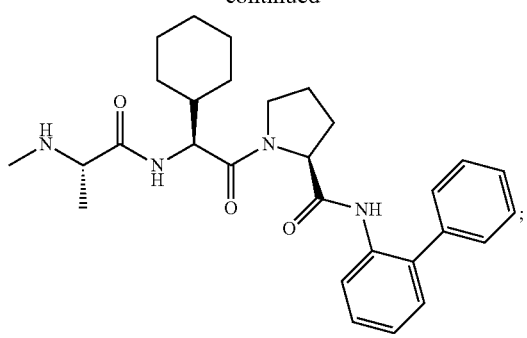
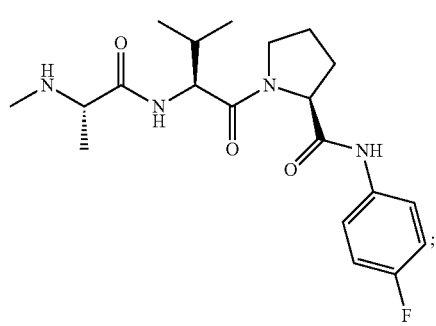
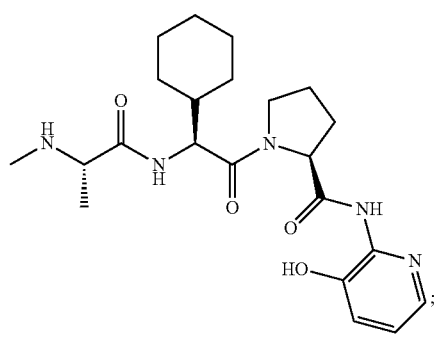
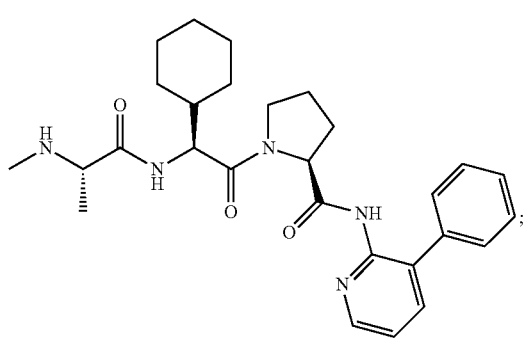
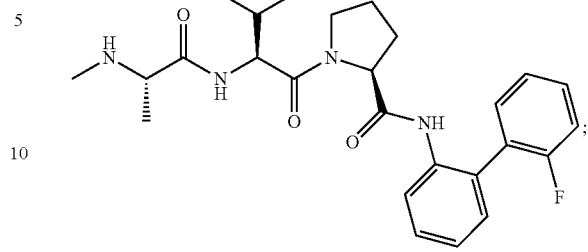
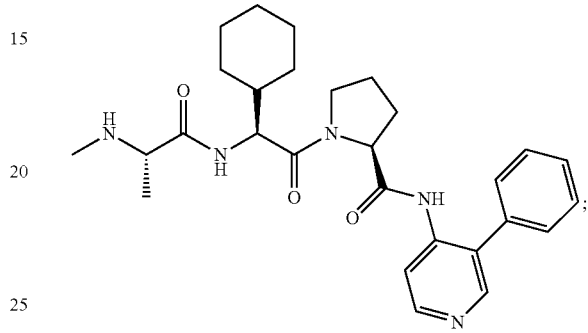
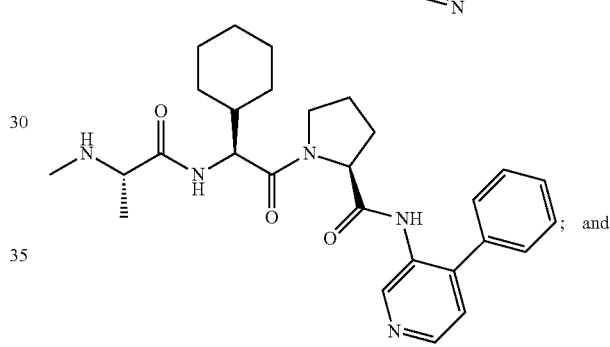
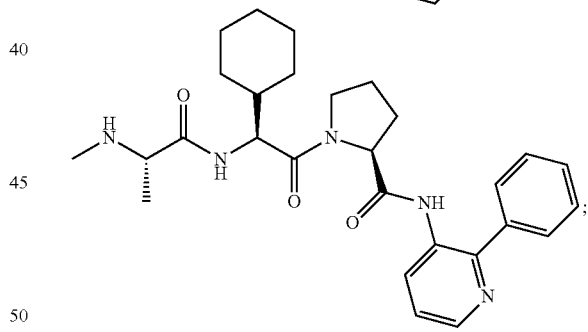
and pharmaceutically acceptable salts thereof.
11. The compound of claim 1, wherein ring A is substituted phenyl, pyridyl, pyrimidinyl, or pyrazinyl.
12. The compound of claim 1, wherein ring A is substituted 2-pyridyl.
* * * * *